(12) United States Patent
Miki et al.

(10) Patent No.: US 6,437,132 B2
(45) Date of Patent: Aug. 20, 2002

(54) THIENOPYRIDINE DERIVATIVES, THEIR INTERMEDIATES AND PRODUCTION THEREOF

(75) Inventors: Shokyo Miki, Toyonaka; Koichiro Fukuoka, Osaka, both of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/908,507

(22) Filed: Jul. 18, 2001

Related U.S. Application Data

(62) Division of application No. 09/446,542, filed as application No. PCT/JP98/03575 on Aug. 11, 1998.

(30) Foreign Application Priority Data

Aug. 13, 1997 (JP) .............................................. 9-218862
Aug. 13, 1997 (JP) .............................................. 9-218863

(51) Int. Cl.$^7$ .................. C07D 495/04; A61K 31/4365
(52) U.S. Cl. ...................................... 546/114; 514/301
(58) Field of Search .................... 546/114, 80; 514/301

(56) References Cited

U.S. PATENT DOCUMENTS 5,817,819 A 10/1998 Faruya et al. ................ 546/114
5,977,132 A * 11/1999 Sazuki et al. ................ 514/301
6,048,863 A 4/2000 Faruya et al. ................ 546/258

FOREIGN PATENT DOCUMENTS

| EP | 781774 | 7/1997 |
| JP | 9-169766 A | 6/1997 |
| JP | 10-158140 A | 6/1998 |
| WO | WO 97/14697 A1 | 4/1997 |
| WO | WO 97/40846 A1 | 11/1997 |
| WO | WO 97/41126 A1 | 11/1997 |

* cited by examiner

*Primary Examiner*—Alan L. Rotman
*Assistant Examiner*—Rita Desai
(74) *Attorney, Agent, or Firm*—Mark Chao; Elaine M. Ramesh

(57) ABSTRACT

The present invention provides an intermediate for producing a thienopyridine derivative useful as a GnRH antagonist as well as an efficient and safe method for producing the same in an industrial scale at a high yield.

4 Claims, No Drawings

THIENOPYRIDINE DERIVATIVES, THEIR INTERMEDIATES AND PRODUCTION THEREOF

This application is a division of U.S. patent application Ser. No. 09/446,542, now U.S. Pat. No. 6,313,301, issued Nov. 6, 2001, which was the Natigdal Phase filing of International Patent Application No. PCT/JP98/03575, filed Aug. 11, 1998.

TECHNICAL FIELD

The present invention relates to synthetic intermediates for production of compounds having thienopyridine skeleton and being useful for medicines, agricultural chemicals, and so forth, especially thienopyridine derivatives exhibiting gonadotropin releasing hormone (GnRH) antagonizing activity, and their production.

As a basic structure of a thienopyridine, 4,7-dihydro-4-oxo-thieno[2,3-b]pyridine of the formula:

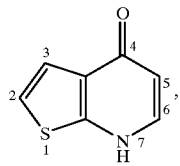

or thieno[2,3-b]pyridine of the formula:.

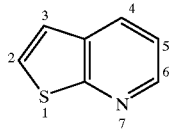

is exemplified.

BACKGROUND ART

Thienopyridines are known to have antibacterial activities as well as other activities found recently such as angiotensine II antagonistic activities and GnRH antagonistic activities, due to which they are expected to be used widely in the fields of medicines and agricultural industries. Concerning the synthetic method for 5-acyl-4-hydroxythieno[2,3-b]pyridine derivative, one of such thienopyridines, there are examples reported on a direct synthesis of 5-acetyl-4-hydroxythieno[2,3-b]pyridine from 2-aminothiophene by a method called Gould-Jacobs method characterized by employing an ethoxymethylene compound of an active methylene compound as shown below [M. A. -Khan et al., J. Heterocyclic Chem., Vol. 14, p. 807 (1977)]:

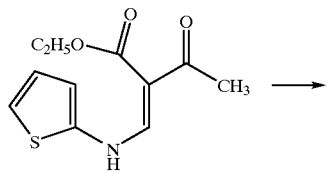

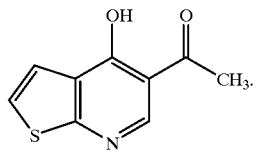

a synthesis from a corresponding acyl group-containing polysubstituted pyridine as shown below (F. A. Abu-Shanab et al., J. Chem. Soc. Perkin Trans. 1, 1994, page 1449):

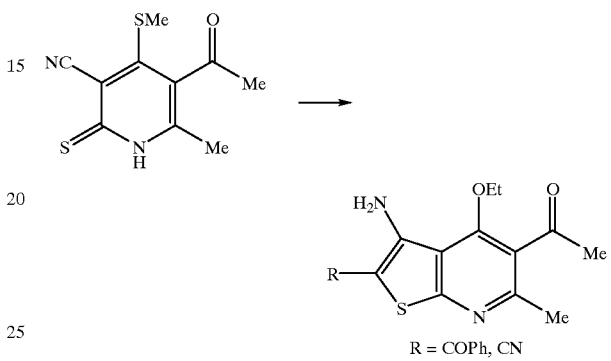

R = COPh, CN and a synthesis through functional group conversion in the 5-position of a 5-ethoxycarbonyl-4-hydroxythieno[2,3-b] pyridine derivative or a 5-cyano-substituted derivative thereof obtained by a conventional procedure as shown below [WO 95/28405 (JP-A-8-295693)]:

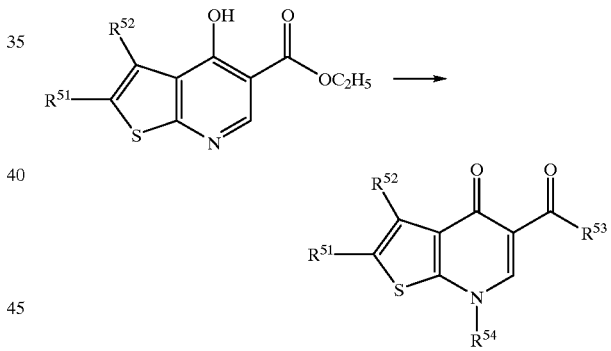

wherein $R^{51}$ represents hydrogen or a group through a carbon, nitrogen, oxygen or sulfur atom, $R^{52}$ represents hydrogen or alkyl, $R^{53}$ a hydrocarbon group, and $R^{54}$ represents phenyl-alkylene which may be substituted.

In order to produce a thienopyridine derivative having a GnRH antagonistic effect, a compound having a nitrophenyl in the 2-position and a halogenomethyl in the 3-position is produced as an intermediate in WO 95/28405 (JP-A-8-295693). In the production of this compound, a nitro group is first introduced into the phenyl of the compound having a phenyl in the 2-position and a methyl in the 3-position and then the methyl in the 3-position is converted into a halogenomethyl.

Also in WO 95/28405 (JP-A-8-295693), a compound having an acid amide in the 5-position is produced from a compound having a carboxylic acid ester in the 5-position.

In the method by M. A. Khan et al. described above, the product is provided via an undesirable step such as the involvement of an organotin compound in an attempt to avoid the formation of an unstable 2-aminothiophene as an intermediate, while the method by F. A. Abu-Shanab et al. provides a O-ethylated product and involves a limitation in terms of the substituents on the thiophene ring, because of which the range of the application is limited.

On the other hand, the method for obtaining a 5-acyl form by the functionality conversion of a 5-ethoxycarbonyl-4-hydroxythieno[2,3-b]pyridine derivative or a 5-cyano-substituted derivative thereof which are obtained by a conventional method involves a less efficient multiple-stage synthesis. In the production of a GnRH antagonistic thienopyridine derivative employing this conventional method disclosed in WO 95/28405 (JP-A-8-295693) involves a large number of the production steps, which also make this method less efficient.

Accordingly, there has still been a desire to develop a method for producing a 5-acyl-4-hydroxythieno[2,3-b] pyridine skeleton conveniently and efficiently.

In the method disclosed in WO 95/28405 (JP-A-8-295693) which involves a conversion of the methyl in the 3-position of a compound having a nitrophenyl in the 2-position and the methyl in the 3-position into a halogenomethyl, carbon tetrachloride is employed as a solvent (see Example 6 in this publication). Since carbon tetrachloride has a high toxicity, an industrial or safety and sanitary consideration encourages to use a method employing no carbon tetrachloride. Nevertheless, no use of carbon tetrachloride results in a disadvantageous intermission of a brominating reaction.

In the method disclosed in WO 95/28405 (JP-A-8-295693), for producing a compound having an acid amide structure in the 5-position from a compound having a carboxylic acid ester in the 5-position, trimethylaluminum is used (see Example 50 in this publication). Since this trimethylaluminum is readily flashing and flammable, highly toxic and should be free from water, it should be handled with a great care. Industrially, a safe production method requiring no use of trimethylaluminum is desired.

DISCLOSURE OF THE INVENTION

We made an effort under the circumstance mentioned above and finally found that by halogenating the methyl in the 3-position of 4,7-dihydro-4-oxothieno[2,3-b]pyridine represented by the formula:

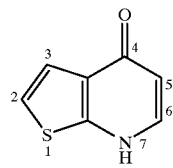

having a phenyl in the 2-position and a methyl in the 3-position followed by introducing a nitro group into the phenyl in the 2-position of a resultant compound, a rapid halogenation in a solvent other than carbon tetrachloride, such as an easily-handled solvent such as ethyl acetate, under a gentle and convenient condition is possible in a halogenation process, and an easily-operable nitration by dissolving said halogenated compound in a solvent such as methanesulfonic acid followed by reacting with various nitrates in a nitration process is also possible.

It is also found that by producing a compound having an acid amide structure in the 5-position from a compound having a free carboxylate in the 5-position a target compound can be produced safely and conveniently in a high yield and a high purity without requiring the use of dangerous trimethylaluminum.

Also, the present inventors found out that a compound of the formula:

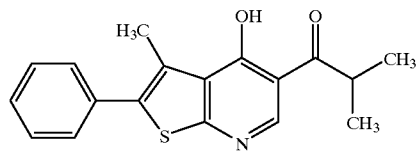

or a salt thereof, is obtained in high yield by subjecting a compound of the formula:

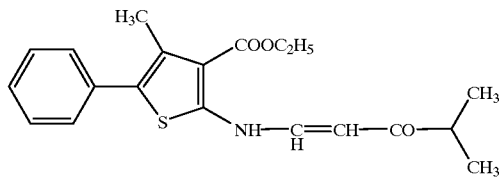

or a salt thereof to cyclization.

The inventors conducted further investigation based on this finding, and developed the present invention.

The present invention, therefore, relates to:

(1) a compound of the formula:

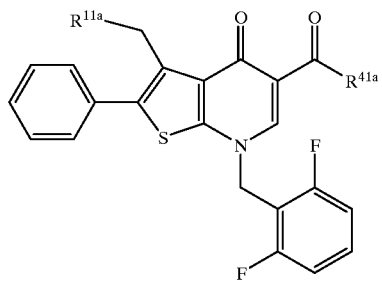

wherein $R^{11a}$ represents hydrogen or halogen, and $R^{41a}$ represents $C_{1-6}$ alkyl, $C_{1-6}$ alkoxy or $C_{6-10}$ aryl, with proviso that $R^{41a}$ is not ethoxy when $R^{11a}$ is hydrogen, or a salt thereof;

(2) a compound of the above (1) or a salt thereof, wherein $R^{11a}$ is hydrogen or bromo;

(3) a compound of the above (1) or a salt thereof, which is 7-(2,6-difluorobenzyl)-4,7-dihydro-5-isobutyryl-3-methyl-4-oxo-2-phenylthieno[2,3-b]pyridine;

(4) a compound of the above (1) or a salt thereof, which is 4 3-bromomethyl-7-(2,6-difluorobenzyl)-4,7-dihydro-5-isobutyryl-4-oxo-2-phenylthieno[2,3-b] pyridine;

(5) a compound of the above (1) or a salt thereof, which is 3-bromomethyl-7-(2,6-difluorobenzyl)-4,7-dihydro-4-oxo-2-phenylthieno[2,3-b]pyridine-5-carboxylic acid ethyl ester;

(6) a process for producing a compound of the formula:

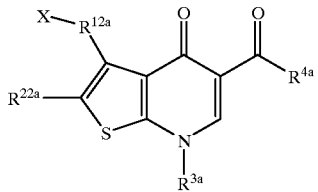

wherein X represents halogen, $R^{12a}$ represents a divalent hydrocarbon group which may be substituted, $R^{3a}$ represents a hydrocarbon group which may be substituted, $R^{4a}$ represents a hydrocarbon group or a hydrocarbon-oxy group, and $R^{22a}$ represents a hydrocarbon group substituted by nitro, or a salt thereof, which comprises subjecting a compound of the formula:

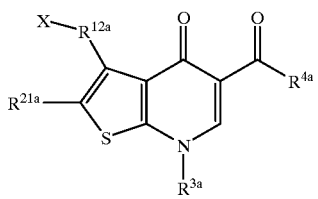

wherein $R^{21a}$ represents a hydrocarbon group and other symbols are as defined above, or a salt thereof to nitration;

(7) a process of the above (6), wherein $R^{12a}$ is methylene, $R^{21a}$ is phenyl, $R^{22a}$ is nitrophenyl, $R^{3a}$ is difluorophenyl-methyl, and $R^{4a}$ is isopropyl or ethoxy;

(8) a process for producing a compound of the formula:

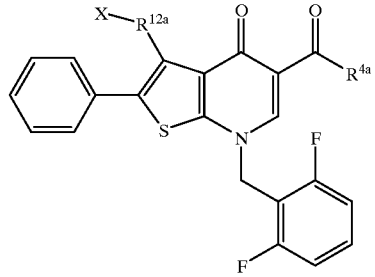

wherein X represents halogen, $R^{12a}$ represents a divalent hydrocarbon group, and $R^{4a}$ represents a hydrocarbon group or a hydrocarbon-oxy group, or a salt thereof, which comprises subjecting a compound of the formula:

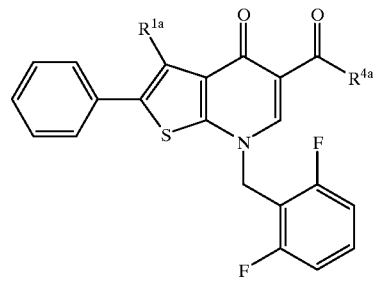

wherein $R^{1a}$ represents a hydrocarbon group which may be substituted and the other symbol is as defined above, or a salt thereof to halogenation;

(9) a process of the above (8), wherein the halogenation is carried out in the presence of methyl acetate;

(10) a process of the above (8), wherein X is bromo, $R^{1a}$ is methyl, $R^{12a}$ is methylene, and $R^{4a}$ is isopropyl or ethoxy;

(11) a process for producing a compound of the formula:

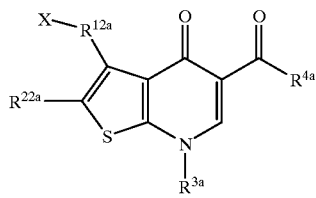

wherein X represents halogen, $R^{12a}$ represents a divalent hydrocarbon group which may be substituted, $R^{3a}$ represents a hydrocarbon group which may be substituted, $R^{4a}$ represents a hydrocarbon group or a hydrocarbon-oxy group, and $R^{22a}$ represents a hydrocarbon group substituted by nitro, or a salt thereof, which comprises subjecting a compound of the formula:

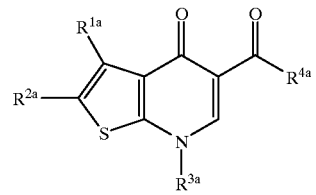

wherein $R^{1a}$ and $R^{2a}$ each represents a hydrocarbon group which may be substituted and other symbols are as defined above, or a salt thereof to halogenation to obtain a compound of the formula:

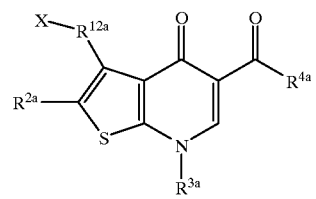

wherein each symbol is as defined above, or a salt thereof, and then subjecting the resultant compound to nitration;

(12) a process of the above (11), wherein $R^{1a}$ is methyl, $R^{12a}$ is methylene, $R^{2a}$ is phenyl, $R^{22a}$ is nitrophenyl, $R^{3a}$ is difluorophenyl-methyl, and $R^{4a}$ is isopropyl or ethoxy;

(13) a process for producing a compound of the formula:

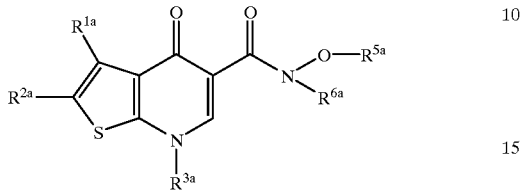

wherein $R^{1a}$, $R^{2a}$ and $R^{3a}$ each represents a hydrocarbon group which may be substituted, and $R^{5a}$ and $R^{6a}$ each represents a hydrocarbon group, or a salt thereof, which comprises reacting compound of the formula:

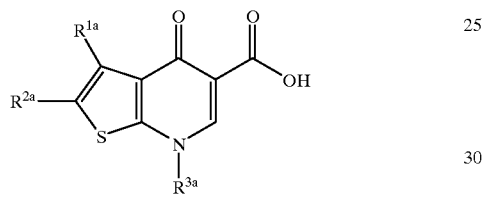

wherein each symbol is as defined above, or a salt thereof with a compound of the formula:

wherein each symbol is as defined above, or a salt thereof;

(14) a process of the above (13), wherein $R^{1a}$ is methyl which may be substituted by N-benzyl-N-methylamino, $R^{2a}$ is phenyl which may be substituted by isobutyrylamino, $R^{3a}$ is difluorophenyl-methyl, and $R^{5a}$ and $R^{6a}$ are methyl;

(15) a compound of the formula:

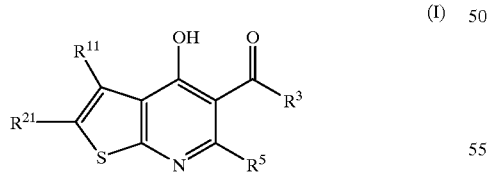

(I)

wherein $R^{11}$ represents $C_{1-6}$ alkyl, $R^{21}$ represents phenyl which may be substituted, or $R^{11}$ and $R^{21}$ form, taken together with adjacent two carbon atoms, a 5- to 7-membered ring which may be substituted, $R^3$ represents a hydrocarbon group which may be substituted, and $R^5$ represents hydrogen or a hydrocarbon group, or a salt thereof;

(16) a compound of the above (15) or a salt thereof, wherein the substituent of the phenyl which may be substituted for $R^{21}$ is isobutyrylamino or methoxy;

(17) a compound of the above (15) or a salt thereof, which is 4-hydroxy-5-isobutyryl-3-methyl-2-phenylthieno[2,3-b]pyridine;

(18) a compound of the above (15) or a salt thereof, which is 4-hydroxy-5-isobutyryl-2-(4-isobutyrylaminophenyl)-3-methylthieno[2,3-b]pyridine;

(19) a process for producing a compound of the formula:

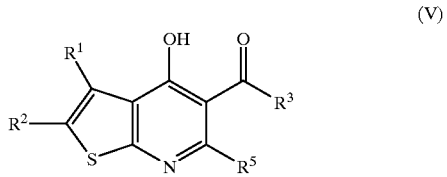

(V)

wherein $R^1$ and $R^2$ each represents a hydrocarbon group which may be substituted, or $R^1$ and $R^2$ form, taken together with adjacent two carbon atoms, a 5- to 7-membered ring which may be substituted, $R^3$ represents a hydrocarbon group which may be substituted, and $R^5$ represents hydrogen or a hydrocarbon group, or a salt thereof, which comprises subjecting a compound of the formula:

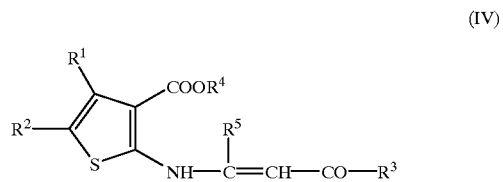

(IV)

wherein $R^4$ represents a hydrocarbon group and other symbols are as defined above, or a salt thereof to cyclization;

(20) a process of the above (19), wherein $R^1$ is methyl, $R^2$ is phenyl which may be substituted by isobutyrylamino or methoxy, or $R^1$ and $R^2$ form, taken together with adjacent two carbon atoms, tetrahydrobenzene ring, $R^3$ is methyl, isopropyl or phenyl, $R^4$ is ethyl, and $R^5$ is hydrogen;

(21) a compound of the formula:

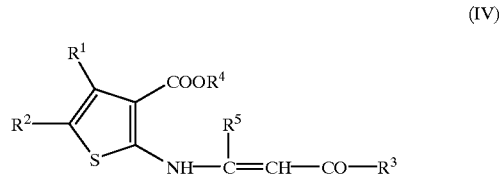

(IV)

wherein $R^1$ and $R^2$ each represents a hydrocarbon group which may be substituted, or $R^1$ and $R^2$ form, taken together with adjacent two carbon atoms, a 5- to 7-membered ring which may be substituted, $R^3$ represents a hydrocarbon group which may be substituted, $R^4$ represents a hydrocarbon group, and $R^5$ represents hydrogen or a hydrocarbon group, or a salt thereof;

(22) a compound of the above (21) or a salt thereof, wherein $R^1$ is methyl, $R^2$ is phenyl which may be substituted by isobutyrylamino, methoxy or nitro, or $R^1$ and $R^2$ form, taken together with adjacent two carbon. atoms, tetrahydrobenzene ring, $R^3$ is methyl, isopropyl or phenyl, $R^4$ is ethyl, and $R^5$ is hydrogen;

(23) a compound of the above (21) or a salt thereof, which is 4-methyl-2-[(4-methyl-3-oxo-1-penten-1-yl)amino]-5-phenylthiophene-3-carboxylic acid ethyl ester;

(24) a compound of the above (21) or a salt thereof, which is 5-(4-isobutyrylaminophenyl)-4-methyl-2-[(4-methyl-3-oxo-1-penten-1-yl)amino]thiophene-3-carboxylic acid ethyl ester;

(25) a process for producing a compound of -the formula:

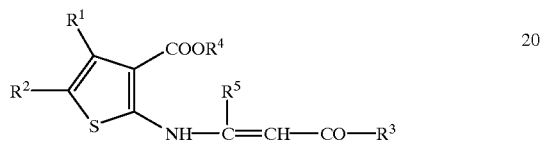

(IV)

wherein $R^1$ and $R^2$ each represents a hydrocarbon group which may be substituted, or $R^1$ and $R^2$ form, taken together with adjacent two carbon atoms, a 5- to 7-membered ring which may be substituted, $R^3$ represents a hydrocarbon group which may be substituted, $R^4$ represents a hydrocarbon group, and $R^5$ represents hydrogen or a hydrocarbon group, or a salt thereof, which comprises reacting a compound of the formula:

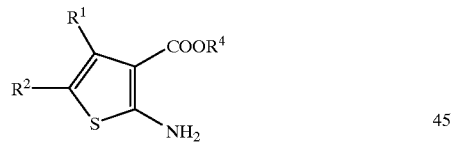

(II)

wherein each symbol is as defined above, or a salt thereof, with a compound of the formula:

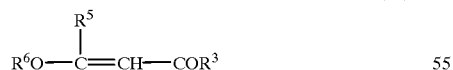

(III)

wherein $R^6$ represents hydrogen, sodium, potassium or a hydrocarbon group and other symbols are as defined above, or a salt thereof;

(26) a process of the above (25), wherein $R^1$ is methyl, $R^2$ is phenyl which may be substituted by isobutyrylamino, methoxy or nitro, or $R^1$ and $R^2$ form, taken together with adjacent two carbon atoms, tetrahydrobenzene ring, $R^3$ is methyl, isopropyl or phenyl, $R^4$ is ethyl, and $R^5$ is hydrogen;

(27) a process for producing a compound of the formula:

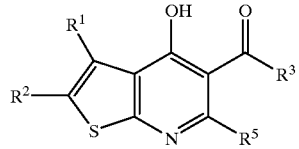

(V)

wherein $R^1$ and $R^2$ each represents a hydrocarbon group which may be substituted, or $R^1$ and $R^2$ form, taken together with adjacent two carbon atoms, a 5- to 7-membered ring which may be substituted, $R^3$ represents a hydrocarbon group which may be substituted, and $R^5$ represents hydrogen or a hydrocarbon group, or a salt thereof, which comprises reacting a compound of the formula:

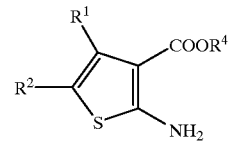

(II)

wherein $R^4$ is a hydrocarbon group, and other symbols are as defined above, or a salt thereof with a compound of the formula:

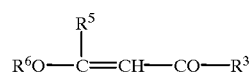

(III)

wherein $R^6$ represents hydrogen, sodium, potassium or a hydrocarbon group, and other symbols are as defined above, or a salt thereof, to obtain a compound of the formula:

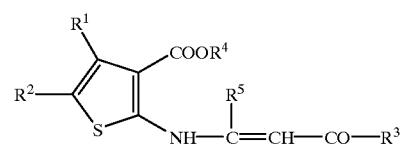

(IV)

wherein each symbol is as defined above, or a salt thereof, and then subjecting the resultant compound to cyclization;

(28) a process of the above (27), wherein $R^1$ is methyl, $R^2$ is phenyl which may be substituted by isobutyrylamino or methoxy, or $R^1$ and $R^2$ form, taken together with adjacent two carbon atoms, tetrahydrobenzene ring, $R^3$ is methyl, isopropyl or phenyl, $R^4$ is ethyl, and $R^5$ is hydrogen;

(29) a compound of the formula:

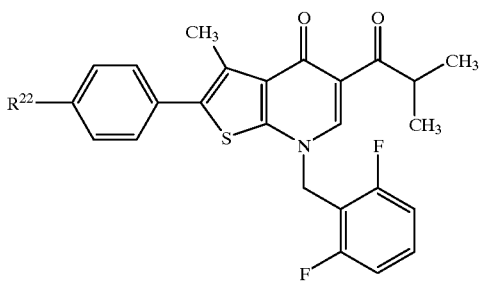

wherein $R^{22}$ represents isobutyrylamino or methoxy, or a salt thereof;

(30) a compound of the above (29) or a salt thereof, which is 7-(2,6-difluorobenzyl)-4,7-dihydro-5-isobutyryl-2-(4-isobutyrylaminophenyl)-3-methyl-4-oxothieno[2,3-b]pyridine;

(31) a process for producing a compound of the formula:

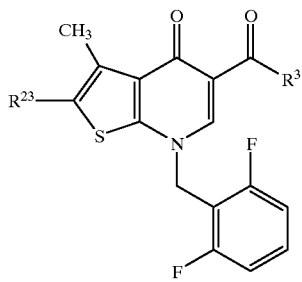

(VI)

wherein $R^{23}$ represents phenyl which may be substituted by isobutyrylamino or methoxy, and $R^3$ represents a hydrocarbon group which may be substituted, or a salt thereof, which comprises reacting a compound of the formula;

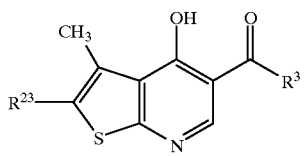

wherein each symbol is as defined above, or a salt thereof, with a compound of the formula:

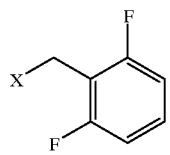

wherein X represents halogen, or a salt thereof; and

(32) a dibasic acid salt of 7-(2,6-difluorobenzyl)-4,7-dihydro-5-isobutyryl-2-(4-aminophenyl)-3-(N-benzyl-N-methylaminomethyl)-4-oxothieno[2,3-b]pyridine.

BEST MODE FOR CARRYING OUT THE INVENTION

In the above formulae, halogen for $R^{11a}$ includes, for example, fluoro, chloro, bromo, iodo. Among others, bromo is especially preferred.

In the above formulae, $C_{1-6}$ alkyl for $R^{41a}$ includes, for example, methyl, ethyl, n-propyl, isopropyl, butyl, isobutyl, sec-butyl, tert-butyl, pentyl, hexyl, and so forth. Among others, $C_{1-3}$ alkyl is preferred.

In the above formulae, $C_{1-6}$ alkoxy for $R^{41a}$ includes, for example, methoxy, ethoxy, n-propoxy, isopropoxy, n-butoxy, isobutoxy, sec-butoxy, t-butoxy, and so forth. Among others, $C_{1-3}$ alkoxy is preferred.

In the above formulae, $C_{6-10}$ aryl for $R^{41a}$ includes, for example, phenyl, 1-naphthyl, 2-naphthyl, and so forth. Among others, phenyl is preferred.

In the above formulae, halogen for X includes, for example, fluoro, chloro, bromo, iodo. Amongothers, bromo is especially preferred.

In the above formulae, preferred is a $C_{1-20}$ hydrocarbon group as the hydrocarbon group of the hydrocarbon group which may be substituted for $R^{1a}$, $R^{2a}$ or $R^{3a}$, the hydrocarbon group for $R^{4a}$, $R^{5a}$ or $R^{6a}$, and the hydrocarbon group of the hydrocarbon-oxy for $R^{4a}$.

The above $C_{1-20}$ hydrocarbon group includes, for example, (1) $C_{1-15}$ alkyl (e.g., methyl, ethyl, n-propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc., preferably $C_{1-6}$ alkyl, etc.), (2) $C_{3-10}$ cycloalkyl (e.g., cyclopropyl, cyclobutyl, cyclopentyl, cyclohexyl, cycloheptyl, cyclooctyl, cyclononyl, etc.), (3) $C_{2-10}$ alkenyl (e.g., vinyl, allyl, 1-butenyl, 2-butenyl, butadienyl, isopropenyl, 2-methylallyl, hexatrienyl, 3-octenyl, etc.), (4) $C_{2-10}$ alkynyl (e.g., ethynyl, propargyl, 2-propynyl, isopropynyl, 2-butynyl, 3-hexynyl, etc.), (5) $C_{3-10}$ cycloalkenyl (e.g., cyclopropenyl, cyclopentenyl, cyclohexenyl), (6) $C_{6-14}$ aryl (e.g., phenyl, naphthyl, anthryl, phenanthryl, acenaphthyl, anthracenyl, etc.), (7) $C_{7-19}$ aralkyl ($C_{6-14}$ aryl-$C_{1-6}$ alkyl such as benzyl, phenethyl, benzhydryl, and trityl), and so forth.

The divalent hydrocarbon group of the divalent hydrocarbon group which may be substituted for $R^{12a}$, includes preferably, for example, a divalent $C_{1-20}$ hydrocarbon group such as (1) $C_{1-15}$ alkylene (e.g., methylene, ethylene, n-propylene, isopropylene, butylene, isobutylene, sec-butylene, pentylene, and hexylene, preferably $C_{1-6}$ alkylene, etc.), (2) $C_{2-10}$ alkenylene (e.g., vinylene, allylene, 1-butenylene, 2-butenylene, butadienylene, isopropenylene, 2-methylallylene, hexatrienylene, 3-octenylene, etc., preferably-$C_{2-6}$ alkenylene), (3) $C_{2-10}$ alkynylene (e.g., ethynylene, propargylene, 2-propynylene, isopropynylene, 2-butynylene, 3-hexynylene, etc., preferably $C_{2-6}$ alkynylene), and so forth.

The hydrocarbon group which may be substituted for $R^{1a}$, $R^{2a}$ or $R^{3a}$, and the divalent hydrocarbon group which may be substituted for $R^{12a}$ may have 1 to 6, preferably 1 to 5, more preferably 1 to 3, especially 1 or 2 substituents at possible positions of the hydrocarbon group.

The substituents of the hydrocarbon group which may be substituted for $R^{1a}$, $R^{2a}$ or $R^{3a}$, include, for example, (1)

halogen (e.g., fluoro, chloro, bromo, and iodo), (2) nitro, (3) nitroso, (4) cyano or isocyano, (5) amino which may be substituted [e.g., an amino of the formula: —NR$^{30a}$R$^{31a}$ wherein R$^{30a}$ and R$^{31a}$ each represents hydrogen, C$_{1-10}$ alkyl, C$_{3-10}$ cycloalkyl, C$_{2-10}$ alkenyl, C$_{6-14}$ aryl, C$_{7-19}$ aralkyl (C$_{6-14}$ aryl-C$_{1-5}$ alkyl, etc.), C$_{1-10}$ acyl (C$_{1-10}$ alkanoyl), C$_{1-6}$ alkoxy-carbonyl, C$_{1-6}$ alkylthio, C$_{1-6}$ alkylsulfonyl, C$_{1-6}$ alkylsulfinyl or a heterocyclic group (a 5- to 8-membered saturated or unsaturated heterocyclic group containing 1 to 4 hetero atoms selected from the group consisting of oxygen, sulfur and nitrogen atoms, or a condensed heterocyclic group thereof, as mentioned below)], (6) hydroxy which may be substituted by substituent(s) selected from the group consisting of (i) C$_{1-6}$ alkyl [this C$_{1-6}$ alkyl may be substituted by halogen, hydroxy, C$_{1-6}$ alkoxy, C$_{2-10}$ alkenyl, C$_{3-10}$ cycloalkyl, C$_{1-3}$ alkylthio, C$_{1-6}$ alkylcarbonyl, carboxy, carbamoyl, C$_{1-6}$ alkyl-carbamoyl, a heterocyclic group (a 5- to 8-membered saturated or unsaturated heterocyclic group containing 1 to 4 hetero atoms selected from the group consisting of oxygen, sulfur and nitrogen atoms, or a condensed heterocyclic group thereof, as mentioned below) or halogen], (ii) C$_{1-4}$ acyl (C$_{1-4}$ alkanoyl), (iii) C$_{7-19}$ aralkyl (C$_{6-14}$ aryl-C$_{1-5}$ alkyl; this group may be substituted by halogen, C$_{1-3}$ alkoxy or C$_{1-4}$ alkyl), (iv) C$_{6-14}$ aryl (this may be substituted by halogen), (v) C$_{2-6}$ alkenyl, (vi) C$_{3-7}$ cycloalkyl, (vii) C$_{1-3}$ alkoxycarbonyl, (viii) mono- or C$_{1-6}$ alkylamino, (ix) C$_{2-6}$ alkenylamino, (x) C$_{1-6}$ alkylcarbonyl, (xi) C$_{3-6}$ cycloalkyloxycarbonyl, and (xii) trifluorosulfonyl, (7) a group of the formula: —S(O) n —R$^{32a}$ wherein n represents an integer of 0 to 2, and R$^{32a}$ represents hydrogen or a hydrocarbon group which may be substituted by substituents such as halogen, nitro, cyano, hydroxy, oxo, thioxo, carboxy, cyano-C$_{6-14}$ aryl, halogeno-C$_{6-14}$ aryl, etc.; in this hydrocarbon group, C$_{1-20}$ hydrocarbon group is preferred, especially, C$_{1-6}$ alkyl, C$_{6-14}$ aryl, and C$_{7-19}$ aralkyl (C$_{6-14}$ aryl-C$_{1-5}$ alkyl) are preferred, (8) carbamoyl which may be substituted (the substituents of this carbamoyl include, for example, mono- or di-C$_{1-6}$ alkyl, preferably mono- or di-C$_{1-3}$ alkyl, etc.), (9) a group through carbonyl [e.g., a group of the formula: —CO—R$^{33a}$ wherein R$^{33a}$ represents (i) hydrogen, (ii) hydroxy, (iii) C$_{1-6}$ alkyl, (iv) C$_{1-6}$ alkoxy (this alkoxy may be substituted by C$_{6-14}$ aryl which may be substituted by halogen or nitro, etc.), (v) C$_{3-6}$ cycloalkyl, (vi) C$_{6-14}$ aryl, (vii) C$_{7-19}$ aralkyl (C$_{6-14}$ aryl-C$_{1-6}$ alkyl), (viii) amino which may be substituted (e.g. the above amino) or (ix) a heterocyclic group (a 5- to 8-membered saturated or unsaturated heterocyclic group containing 1 to 4 hetero atoms selected from the group consisting of oxygen, sulfur and nitrogen atoms, or a condensed heterocyclic group thereof, as mentioned below)], (10) a 5- to 8-membered saturated or unsaturated heterocyclic group containing 1 to 4 hetero atoms selected from the group consisting of oxygen, sulfur and nitrogen atoms, or a condensed heterocyclic group thereof, as mentioned below, (this heterocyclic group may be substituted by (i) halogen, (ii) C$_{1-4}$ alkyl, (iii) C$_{1-3}$ alkoxy, (iv) C$_{1-4}$ alkylthio, or (v) phenoxy which may be substituted by halogen), (11) sulfo, (12) C$_{6-14}$ aryl (e.g., phenyl, naphthyl, anthryl, phenanthryl, acenaphthyl, anthracenyl, etc.; this aryl may be substituted by 1 to 4 substituents selected from the group consisting of (a) hydroxy, (b) amino, (c) mono- or di-C$_{1-6}$ alkylamino (e.g., methylamino, ethylamino, propylamino, dimethylamino, diethylamino, etc.), (d) C$_{1-6}$ alkoxy (e.g., methoxy, ethoxy, propoxy, hexyloxy, etc.) and (e) halogen (fluoro, chloro, bromo and iodo ), (13) aryloxy [this aryl is same as the above (12)], (14) C$_{3-7}$ cycloalkyl, (15) C$_{1-6}$ alkylenedioxy (e.g., methylenedioxy, ethylenedioxy, propylenedioxy, etc.), (16) oxo, (17) thioxo, (18) C$_{3-4}$ alkynyl (e.g., propargyl, 2-butynyl, etc.), (19) C$_{3-10}$cycloalkyl, (20) C$_{2-10}$ alkenyl (e.g., vinyl, allyl, isopropenyl, 1-butenyl, 2-butenyl, butadienyl, hexatrienyl, 3-octenyl, etc.; C$_{2-6}$ alkenyl is preferred.), (21) C$_{7-19}$ aralkyl (C$_{6-14}$ aryl-C$_{1-6}$ alkyl), (22) amidino, (23) azido, and so forth.

The substituents of the above-mentioned hydrocarbon group which may be substituted, may further have 1 to 3, preferably 1 or 2 substituents at possible positions. Said substituents, which the substituents may further have, include, for example, 1 to 4, preferably 1 or 2 substituents selected from the group consisting of (1) hydroxy, (2) amino, (3) mono- or di-C$_{1-4}$ alkylamino (e.g., methylamino, ethylamino, propylamino, dimethylamino, diethylamino etc.), (4) C$_{1-4}$ alkoxy, preferably C$_{1-3}$ alkoxy (e.g., methoxy, ethoxy, propoxy, etc.), (5) halogen (fluoro, chloro, bromo, andiodo), and nitro, and so forth.

When the hydrocarbon group is cycloalkyl, alkenyl, alkynyl, cycloalkenyl, aryl or aralkyl, this hydrocarbon group may be substituted by 1 to 3 C$_{1-6}$ alkyl, preferably C$_{1-4}$ alkyl (e.g., methyl, ethyl, propyl, isopropyl, butyl, etc.), and this C$_{1-6}$ alkyl may be further substituted by 1 to 3 hydroxy, oxo, C$_{1-3}$ alkoxy (e.g., methoxy, ethoxy, ethoxy, n-propoxy, isopropoxy etc.), C$_{1-3}$ alkylthio, halogen, and carbamoyl, etc.

The substituted C$_{1-6}$ alkyl includes formyl (methyl substituted by an oxo), carboxy (methyl substituted by an oxo and a hydroxy), C$_{1-6}$ alkoxycarbonyl (methyl substituted by an oxo and an alkoxy) (e.g., C$_{1-6}$ alkoxycarbonyl such as methoxycarbonyl, ethoxycarbonyl, t-butoxycarbonyl, etc.), hydroxy-C$_{1-6}$ alkyl (e.g., hydroxymethyl, hydroxyethyl, hydroxybutyl, hydroxypropyl, etc.), C$_{1-3}$ alkoxy-C$_{1-6}$ alkyl (e.g., methoxymethyl, ethoxymethyl, ethoxybutyl, propoxymethyl, prbpoxyhexyl, etc.), and so forth.

The number of the above substituents is 1 to 6, preferably 1 to 5, more preferably 1 to 3, especially 1 or 2. The number of the substituents which substituents may further have, is 1 to 3, preferably 1 to 2.

In the definitions of the above-mentioned groups, C$_{1-10}$ alkyl includes, for example, methyl, ethyl, propyl, isopropyl, butyl, isobutyl, sec-butyl, t-butyl, pentyl, isopentyl, neopentyl, hexyl, etc. Among others, preferred is C$_{1-6}$ alkyl, and more preferred is C$_{1-4}$ alkyl or C$_{1-3}$ alkyl. The C$_{1-6}$ alkyl includes, for example, methyl, ethyl, n-propyl, isopropyl, n-butyl, isobutyl, sec-butyl, t-butyl, pentyl, isopentyl, neopentyl, hexyl, etc. The C$_{1-4}$ alkyl includes, for example, methyl, ethyl, n-propyl, isopropyl, n-butyl, isobutyl, sec-butyl and t-butyl. The C$_{1-3}$ alkyl includes, for example, methyl, ethyl, n-propyl, and isopropyl.

In the definitions of the above-mentioned groups, as cycloalkyl preferred is C$_{3-10}$ cycloalkyl such as cyclopropyl, cyclobutyl, cyclopentyl, cyclohexyl, cycloheptyl, cyclooctyl, cyclononyl, etc. Among others, C$_{3-7}$ cycloalkyl (e.g., cyclopropyl, cyclobutyl, cyclopentyl, cyclohexyl, cycloheptyl etc.), and $C_{3-6}$ cycloalkyl (e.g., cyclopropyl, cyclobutyl, cyclopentyl, cyclohexyl, etc.) are preferred.

In the definitions of the above-mentioned groups, $C_{2-10}$ alkenyl includes, for example, vinyl, allyl, 1-butenyl, 2-butenyl, butadienyl, isopropenyl, 2-methylallyl, hexatrienyl, 3-octenyl, etc. Among others, preferred is $C_{2-6}$ alkenyl (e.g., vinyl, allyl, 1-butenyl, 2-butenyl, butadienyl, isopropenyl, 2-methylallyl, hexatrienyl etc.).

In the definitions of the above-mentioned groups, $C_{6-14}$ aryl includes, for example, phenyl, naphthyl, anthryl, phenanthryl, acenaphthyl, anthracenyl, etc.

In the definitions of the above-mentioned groups, $C_{7-19}$ aralkyl includes, for example, $C_{6-14}$ aryl-$C_{1-5}$ alkyl such as benzyl, phenethyl-, benzhydryl, and trityl.

In the definitions of the above-mentioned groups, $C_{1-6}$ alkoxy includes, for example, methoxy, ethoxy, n-propoxy, isopropoxy, n-butoxy, isobutoxy, sec-butoxy, t-butoxy, etc. Among others, $C_{1-4}$alkoxy or $C_{1-3}$ alkoxy (e.g., methoxy, ethoxy, n-propoxy, and isopropoxy) is preferred.

In the definitions of the above-mentioned groups, $C_{1-10}$ acyl includes, for example, $C_{1-10}$ alkanoyl (e.g., formyl, acetyl, propynyl, butyryl, isobutyryl, valeryl, andhexanoyl). Amongo thers, preferred is $C_{1-4}$ acyl [e.g., $C_{1-4}$ alkanoyl (e.g., formyl, acetyl, propionyl, butyryl, isobutyryl, etc.)].

In the definitions of the above-mentioned groups, the heterocyclic group includes, for example, a 5- to 8-membered saturated or unsaturated heterocyclic group containing 1 to 4 hetero atoms selected from the group consisting of oxygen, sulfur and nitrogen atoms, or a condensed heterocyclic group thereof.

The examples of the above heterocyclic group include (1) a 5-membered heterocyclic group containing 1 to 4 hetero atoms selected from the group consisting of oxygen, sulfur and nitrogen atoms in addition to carbon atoms, such as 2- or 3-thienyl, 2- or 3-furyl, 2- or 3-pyrrolyl, 2-, 4- or 5-oxazolyl, 2-,4- or 5-thiazolyl, 3-,4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, succinimido, etc., (2) a 6-membered heterocyclic group containing 1 to 4 hetero atoms selected from the group consisting of oxygen, sulfur and nitrogen atoms in addition to carbon atoms, such as 2-, 3- or 4-pyridyl, 2-, 4- or 5-pyrimidinyl, 2-, 4- or 5-pyrimidinyl, thiomorpholinyl, morpholinyl, oxoimidazinyl, triazinyl, pyrrolidinyl, piperidinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, pyrazinyl, 3- or 4-pyridazinyl, etc., (3) a bi- or tri-cyclic condensed heterocyclic group containing 1 to 4 hetero atoms selected from the group consisting of oxygen, sulfur and nitrogen atoms in addition to carbon atoms, such as benzofuryl, benzothiazolyl, benzoxazolyl, tetrazolo[1,5-b]pyridazinyl, triazolo[4,5-b]pyridazinyl, benzimidazolyl, quinolyl, isoquinolyl, cinnolinyl, phthalazinyl, quinazolinyl, quinoxalinyl, indolizinyl, quinolizinyl, 1,8-naphthylizinyl, purinyl, pteridinyl, dibenzofuranyl, carbazolyl, acridinyl, phenanthridinyl, cromanyl, banzoxazinyl, phenazinyl, phenothiazinyl, phenoxazinyl, phthalimido, etc.

Preferable examples of the above heterocyclic group include imidazolyl, oxazolyl, isoxazolyl, thiazolyl, 1,4-thiazinyl, imidazolinyl, succinimido, phthalimido, etc.

Preferred examples of the substituents of the hydrocarbon group which may be substituted for $R^{1a}$ include (1) nitro, (2) amino whichmay be substituted by $C_{1-10}$ alkyl, $C_{1-10}$ acyl ($C_{1-10}$ alkanoyl) or $C_{1-6}$ alkoxy-carbonyl, etc., (3) hydroxy which may be substituted by $C_{1-6}$ alkyl, $C_{1-4}$ acyl ($C_{1-4}$ alkanoyl), $C_{1-3}$ alkoxy-carbonyl, $C_{1-6}$ alkylcarbonyl, $C_{3-6}$ cycloalkyl-oxycarbonyl or trifluorosulfonyl, etc., (4) a group of the formula: —S(O) n —$R^{32a}$ wherein n represents an integer of 0 to 2, and $R^{32a}$ represents hydrogen or a $C_{1-10}$ hydrocarbon group (preferably $C_{1-6}$ alkyl), (5) succinimido, (6) phthalimido, and so forth.

$R^{1a}$ preferably is (1) a $C_{1-20}$ hydrocarbon group (preferably $C_{1-6}$ alkyl), and (2) a $C_{1-20}$ hydrocarbon group (preferably $C_{1-6}$ alkyl) substituted by (i) amino which may be substituted by $C_{1-1}$ alkyl, $C_{1-10}$ acyl ($C_{1-10}$ alkanoyl) or $C_{1-6}$ alkoxy-carbonyl, (ii) succinimido or (iii) phthalimido. More preferably, $R^{1a}$ is (1) $C_{1-6}$ alkyl, and (2) N—$C_{7-19}$ aralkyl-N—$C_{1-6}$ alkylamino-$C_{1-6}$ alkyl (N—$C_{6-14}$ aryl-$C_{1-6}$ alkyl-N—$C_{1-6}$ alkylamino-$C_{1-6}$ alkyl), etc.

Preferred examples of the substituents of the hydrocarbon group which may be substituted for $R^{2a}$ include (1) nitro, (2) halogen, (3) amino which may be substituted by $C_{1-10}$ acyl ($C_{1-10}$ alkanoy) or $C_{1-6}$ alkoxy-carbonyl, (4) hydroxy which may be substituted by $C_{1-6}$ alkyl, $C_{1-4}$ acyl ($C_{1-4}$ alkanoyl), $C_{1-3}$ alkoxy-carbonyl, $C_{1-6}$ alkylcarbonyl, $C_{3-6}$ cycloalkyl-oxycarbonyl or trifluorosulfonyl, (5) a group of the formula: —S(O) n —$R^{32a}$ wherein n represents an integer of 0 to 2, and $R^{32a}$ represents hydrogen or a $C_{1-6}$ hydrocarbon group which may be substituted (preferably $C_{1-6}$ aryl), (6) carbamoyl, (7) a group through carbonyl (e.g., $C_{1-6}$ alkoxy-carbonyl, etc.), (8) succinimido, (9) phthalimido, and so forth.

$R^{2a}$ preferably is (1) a $C_{1-20}$ hydrocarbon group (preferably $C_{1-6}$ alkyl or $C_{6-10}$ aryl), and (2) a $C_{1-20}$ hydrocarbon group (preferably $C_{1-6}$ alkyl or $C_{6-10}$ aryl, more preferably $C_{6-10}$ aryl) substituted by (i) amino which may be substituted by $C_{1-10}$ acyl ($C_{1-10}$ alkanoyl) or $C_{1-6}$ alkoxy-carbonyl, (ii) hydroxy which may be substituted by $C_{1-6}$ alkyl, $C_{1-4}$ acyl ($C_{1-4}$ alkanoyl), $C_{1-3}$ alkoxy-carbonyl, $C_{1-6}$ alkylcarbonyl or $C_{3-6}$ cycloalkyl-oxycarbonyl, etc., (iii) succinimido or (iv) phthalimido. More preferably, $R^{2a}$ is (1) $C_{6-14}$ aryl, (2) $C_{1-8}$ alkanoylamino-$C_{6-14}$ aryl, (3) $C_{2-10}$ alkenyl-$C_{1-6}$ alkoxy-$C_{6-14}$ aryl, and so forth.

Preferred examples of the substituents of the hydrocarbon group which may be substituted for $R^{3a}$ include (1) nitro, (2) halogen, (3) amino which may be substituted, (4) hydroxy which may be substituted, (5) a group of the formula: —S(O) n —$R^{32a}$ wherein n represents an integer of 0 to 2, and $R^{32a}$ represents hydrogen or a $C_{1-20}$ hydrocarbon group which may be substituted (preferably $C_{1-6}$ alkyl), (6) carbamoyl which may be substituted, (7) a group through carbonyl (e.g., $C_{1-6}$ alkoxy-carbonyl, etc.), and so forth.

Especially $R^{3a}$ preferably is, phenyl-$C_{1-3}$ alkyl which may be substituted by halogen.

Preferred examples of the divalent hydrocarbon group which may be substituted for $R^{12a}$ include $C_{1-6}$ alkylene. More preferred is methylene or ethylene.

Preferred examples of the hydrocarbon group for $R^{4a}$ or the hydrocarbon group of the hydrocarbon-oxy for $R^{4a}$ include $C_{1-6}$ alkyl.

Preferred examples of the hydrocarbon group of the hydrocarbon group substituted by nitro for $R^{22a}$ include $C_{1-6}$ alkyl.

Preferred examples of the hydrocarbon group for $R^{5a}$ or $R^{6a}$ include $C_{1-6}$ alkyl.

$R^{11a}$ preferably is hydrogen or halogen (preferably bromo, etc.).

$R^{41a}$ preferably is $C_{1-6}$ alkyl, $C_{1-6}$ alkoxy, and phenyl. More preferred is $C_{1-3}$ alkyl, ethoxy, phenyl, and so forth.

The following are processes of the present invention.

1. Halogenation in the present invention is carried out by reacting a material compound of the formula:

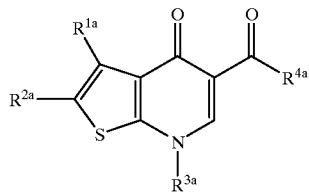

wherein each symbols is as defined above, with a halogenating reagent to obtain a compound of the formula:

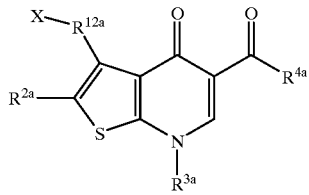

wherein each symbols is as defined above.

The halogenating reagent includes N-halosuccinimide (e.g., N-bromosuccinimide, N-bromophthalimide, 1,3-dibromo-5,5-dimethylhydantoin), etc.

In this reaction, a radical initiator is advantageously used. The radical initiator includes, for example, 2,2'-azobisisobutyronitrile, benzoyl peroxide, 2,2'-azobis(2,4-dimethylvaleronitrile), and so forth.

The amount of the halogenating reagent to be used is about 1 to 1.5 mol, preferably about 1 to 1.2 mol relative to one mol of the material compound. The amount of the radical initiator to be used is about 0 to 0.5 mol, preferably 0.01 to 0.1 mol relative to one mol of the material compound.

In this reaction, a solvent is advantageously used. There is no particular limitation on the kind of solvent that can be used unless the reaction is interfered with. Among others, preferably used are hydrocarbons (e.g., n-hexane, benzene, toluene, xylene, etc.), esters (e.g., ethyl acetate, methyl acetate, etc.), and mixtures of those solvents.

The reaction time is advantageously from about 10 minutes to 5 hours, preferably from 1 to 3 hours. The reaction temperature is selected according to boiling point of the solvent that can be used in the reaction, for example, about 35° C. to reflux temperature, preferably about 70° C. to reflux temperature, more preferably about 70 to 80° C. When methyl acetate is used, the reaction temperature is about 40° C. to reflux temperature, preferably about 50 to 60° C. When ethyl acetate is used, the reaction temperature is, for example, about 40° C. to reflux temperature, preferably about 70° C. to reflux temperature, more preferably bout 70 to 80° C.

2. Nitration in the present invention is carried out by subjecting a material compound of the formula:

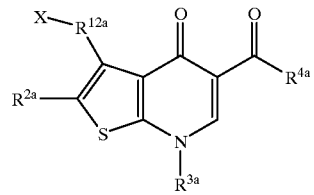

wherein each symbol is as defined above, to nitration to obtain a compound of the formula:

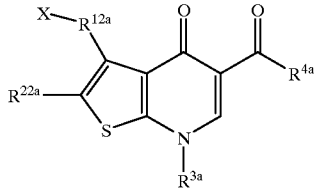

wherein each symbol is as defined above.

Said nitration is carried out according to an ordinary nitration method of aromatic compound. In this reaction, as a nitrating agent, (1) nitric acid, alkali metal of nitric acid (e.g., sodium nitrate, potassium nitrate, etc.) or ammonium salt of nitric acid (e.g., ammonium nitrate, etc.), or mixture with a strong acid is added. As for said strong acid, any acid may be used as far as it can generate nitronium ion from nitric acid. Among them, sulfuric acid, benzenesulfonic acid, toluenesulfonic acid, methanesulfonic acid and trifluoromethanesulfonic acid, which have a high solubility against organic compound, are preferable and used as solvents at the same time.

At addition, it is preferable to drop said nitrating agent comprising 1 mole of nitric acid or nitrate to said strong acid solution of 1 mole of a material compound under said temperature.

This reaction may be carried out without a solvent or in the presence of a solvent. When a solvent is used, the solvent includes, for example, ketones (e.g., acetone, methyl ethyl ketone, etc.), nitriles (e.g., acetonitrile, etc.), sulfoxides (e.g., dimethylsulfoxide, etc.), amides (N,N-dimethylformamide, N,N-dimethylacetamide, etc.), esters (e.g., ethyl acetate, etc.), carboxylic acids (e.g., acetic acid, propionic acid), dimethoxyethane, etc., and mixtures of those solvents.

The reaction temperature is about −40 to 40° C., preferably about 0 to 20° C. The reaction time is about 10 minutes to 10 hours, preferably 1 to 2 hours.

3. The reaction of converting a carboxylic acid derivative to a N-substituted amide derivative, of the present invention is carried out by reacting a material compound of the formula:

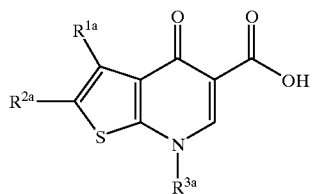

wherein each symbol is as defined above, with a N,O-dihydrocarbonhydroxylamine derivative of the formula:

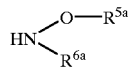

wherein each symbol is as defined above, or salt thereof, to obtain a compound of the formula:

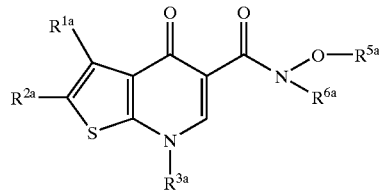

wherein each symbol is as defined above.

In this reaction, the amount of the N,O-dihydrocarbonhydroxylamine derivative or its salt is about 1 to 5 equivalents, preferably 1 to 3 equivalents, relative to one mol of the material compound or its salt.

To this reaction system, advantageously added are about 1 to 5 equivalents, preferably about 1 to 3 equivalents of amines (e.g., triethylamine), about 1 to 5 equivalents, preferably about 1 to 3 equivalents of 1-hydroxybenzotriazole (HOBT), and about 1 to 5 equivalents, preferably 2 to 3 equivalents of 1-ethyl-3-(3-dimethylaminopropyl) carbodiimide (WSC).

This reaction is usually carried out in a solvent that does not interfere with the reaction. Such solvents include, for example, ethers (e.g., dioxane, tetrahydrofuran, 1,2-dimethoxyethane, etc.), ketones (e.g., acetone, etc.), nitriles (e.g., acetonitrile, etc.), amides (e.g., dimethylformamide, dimethylacetamide, etc.), dimethylsulfoxide, sulfolane, etc. and mixtures of those solvents.

This reaction is carried out at about 0 to 100° C., preferably about 50 to 60° C., for about 1 to 10 hours, preferably about 5 to 7 hours.

The material carboxylic acid derivative is obtained by for example, subjecting a compound of the formula:

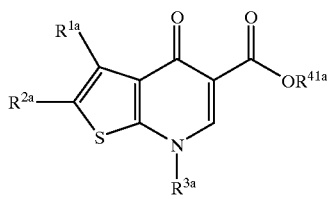

wherein $R^{41a}$ represents a hydrocarbon group and the other symbols are as defined above, which is disclosed in JP-A-8-295693 (WO 95/28405), to hydrolysis.

The hydrolysis is carried out by adding an acid (e.g., hydrochloric acid, sulfuric acid, etc.) or an alkali (e.g., sodium hydroxide, potassium hydroxide, lithium hydroxide, etc.) to the reaction followed by stirring.

The solvents to be used include, for example, water, alcohols (e.g., methanol, ethanol, n-propanol, isopropanol, etc.), tetrahydrofuran, acetone, acetonitrile, 1,2-dimethoxyethane, dioxane, etc.), and so forth. The reaction temperature is usually about 0 to 100° C., preferably about 50 to 80° C. The reaction time is preferably about 0.5 to 10 hours, preferably, about 1 to 4 hours.

4. The reaction of converting the resultant acid amide derivative as mentioned above to a ketone derivative, is carried out by reacting a material compound of the formula:

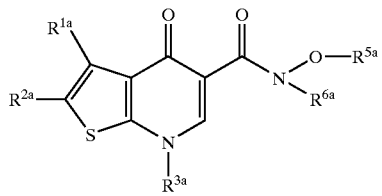

wherein each symbol is as defined above, or a salt thereof with Grignard reagent [e.g., isopropyl magnesium chloride (2M-THF solution), isopropyl magnesium bromide, etc.] to obtain a material compound of the formula:

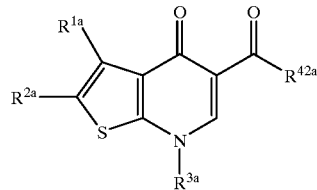

wherein $R^{42a}$ represents a hydrocarbon group and other symbols are as defined above, or a salt thereof.

The amount of the Grignard reagent is about 1 to 10 equivalents, preferably about 2 to 4 equivalents relative to one mol of the material compound or a salt thereof.

This reaction may be carried out in the presence of a solvent, which can be used unless the reaction is interfered with. The solvent includes, for example, the same ones used in the above reaction for obtaining an acid amide derivative.

The reaction temperature is about –10 to 0° C., preferably about –5 to 0° C. The reaction time is about 30 minutes to 5 hours, preferably about 40 to 50 minutes.

Salts of compounds used in these reactions and salts of compounds obtained in these reactions (hereinafter, referred to as "compound of the present invention") are preferably physiologically acceptable acid addition salts. Such salts include, for example, salts with inorganic acids (e.g., hydrochloric acid, phosphoric acid, hydrobromic acid, sulfuric acid, etc.), saltswithorganic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), and so forth. For example, when a compound of the present invention has an acidic group such as carboxylic acid, it may form a physiologically acceptable salt with an inorganic base (e.g., alkali metals or alkaline earth metals such as sodium, potassium, calcium and magnesium, ammonia, etc.) or an organic base (e.g., tri-$C_{1-3}$ alkylamine such as triethylamine, etc.). The compound in free form can be converted to a salt and the one in salt form can be converted to a free form by per se known By methods or analogous thereto.

When the compound has a double bond, and there exist stereoisomers of Z- or E-form, Z-form, E-form and their mixture may be used.

When the compound has a chiral carbon atom, and there exist stereoisomers of R- or S-form, R-form, S-form and their mixture are within the scope of the present invention.

When the compound of the present invention or a salt thereof is an optically active compound, it can be resolved into the d- and l-forms by the conventional optical resolution techniques.

Thus obtained compounds or salt thereof may be isolated and purified by ordinary means of separation such as solvent extraction, concentration under reduced pressure, crystallization, recrystallization, distillation chromatography, and the like.

The compound obtained in the present invention or a salt thereof can be submitted to the next reaction either as the .reaction mixture or after partial purification.

The compound obtained in the present invention or a salt thereof is used for production of thienopyridine derivatives being useful as GnRH antagonists, according to the methods described in, for example, JP-A-8-295693 (WO 95/28405) or analogous methods thereto.

Therefore, the compound obtained in the present invention or a salt thereof can be used as synthetic intermediates for thienopyridine derivatives being useful as GnRH antagonists, which is described in, for example, JP-A-8-295693 (WO 95/28405).

Material compounds and salts thereof used in methods of the present invention can be produced, for example, by the methods described in WO 95/28405 (JP-A-8-295693) or analogous methods thereto.

In the above formulae, $C_{1-6}$ alkyl for $R^{11}$ includes, for example, methyl, ethyl, n-propyl, isopropyl, butyl, isobutyl, sec-butyl, tert-butyl, pentyl, hexyl, etc., preferably methyl, ethyl, n-isopropyl, more preferably methyl.

In the above formulae, the 5- to 7-membered ring of the "5- to 7-membered ring which may be substituted" which $R^{11}$ and $R^{21}$ form, taken together with adjacent two carbon atoms, and the 5- to 7-membered ring of the "5- to 7-membered ring which may be substituted" which $R^1$ and $R^1$ form, taken together with adjacent two carbon atoms include a 5- to 7-membered ring which may contain 1 to 4 nitrogen atoms, sulfur atoms and/or oxygen atoms. Such examples are (1) a ring of the formula:

wherein $R^7$ represents —(CH$_2$)$_3$—, —(CH$_2$)$_4$—, —(CH$_2$)$_5$—, —C=C—C=C—, —CH$_2$—R$^8$—CH$_2$—, —R$^8$—CH$_2$—CH$_2$—, —CH$_2$—CH$_2$—R$^8$—, —CH$_2$—R$^8$—CH$_2$—CH$_2$—, —CH$_2$—CH$_2$— R$^8$—CH$_2$—, —R$^8$—CH$_2$—CH$_2$—CH$_2$—, —CH$_2$— CH$_2$—CH$_2$—R$^8$—, —CH$_2$—R$^8$—CH$_2$—CH$_2$—, —CH$_2$—CH$_2$—R$^8$—CH$_2$—, —CH$_2$—CH$_2$— CH$_2$—, —CH$_2$—CH$_2$—CH$_2$—R$^8$— wherein R$^8$ represents (i) —NH—, (ii) —S(O) m — wherein m represents an integer of 0 to 2, or (iii) —O—, (2) a 5-membered heterocycle containing 1 to 4 hetero atoms selected form oxygen atom, sulfur atom, nitrogen atom, etc., in addition to carbon atoms, such as thiophene, furan, oxazole, thiazole, pyrazole, imidazole, isoxazole, isothiazole, 1,2,3-thiadiazole, 1,2,5-thiadiazole, 1,2,3-triazole, etc., and (3) a 6-membered heterocycle containing 1 to 4 hetero atoms selected form oxygen atom, sulfur atom, nitrogen atom, etc., in addition to carbon atoms, such as pyridine, pyridazine, pyrimidine, triazine, pyrrolidine, pyran, pyrazine, etc.

Substituents which the 5- to 7-membered ring may have include halogen, $C_{1-6}$ alkyl, $C_{1-4}$ alkoxy, nitro, oxo, thioxo, alkylthio, cyano, $C_{1-6}$ alkylcarbonyl, $C_{1-4}$ alkoxycarbonyl, carbamoyl, mono-$C_{1-6}$ alkylcarbamoyl, di-$C_{1-6}$ alkylcarbamoyl, $C_{1-10}$ acylamino (e.g., $C_{1-10}$ alkanoylamino, etc.), di-$C_{1-6}$ alkylamino, $C_{6-14}$ aryl, $C_{6-14}$ aryloxy, heterocyclic group (the above-mentioned "5- to 8-membered saturated or unsaturated heterocyclic group containing 1 to 4 hetero atoms selected from the group consisting of oxygen, sulfur and nitrogen atoms, or a condensed heterocyclic group thereof"), and so forth.

The above 5- to 7-membered ring may have 1 to 3 substituents above-mentioned at possible positions.

In the above formulae, as the hydrocarbon group of the hydrocarbon group which may be substituted for $R^1$, $R^2$ or $R^3$, and as the hydrocarbon group for $R^4$, $R^5$ or $R^6$, preferred is a $C_{1-20}$ hydrocarbon group.

The $C_{1-20}$ hydrocarbon group includes, for example, (1) $C_{1-15}$ alkyl (e.g., methyl, ethyl, n-propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc.), (2) $C_{3-10}$ cycloalkyl (e.g., cyclopropyl, cyclobutyl, cyclopentyl, cyclohexyl, cycloheptyl, cyclooctyl, cyclononyl, etc.), (3) $C_{2-10}$ alkenyl (e.g., vinyl, allyl, 1-butenyl, 2-butenyl, butadienyl, isopropenyl, 2-methylallyl, hexatrienyl, 3-octenyl, etc.), (4) $C_{2-10}$ alkynyl (e.g., ethynyl, propargyl, 2-propynyl, isopropynyl, 2-butynyl, 3-hexynyl, etc.), (5) $C_{3-10}$ cycloalkenyl (e.g., cyclopropenyl, cyclopentenyl, cyclohexenyl), (6) $C_{6-14}$ aryl (e.g., phenyl, naphthyl, anthryl, phenanthryl, acenaphthyl, anthracenyl, etc.), (7) $C_{7-19}$ aralkyl (e.g., $C_{6-14}$ aryl-$C_{1-5}$ alkyl such as benzyl, phenethyl, benzhydryl, trityl, etc.), and the like.

Substituents of the hydrocarbon group which may be substituted for $R^1$, $R^2$ or $R^3$ include, for example, (1) halogen (e.g.,fluoro,chloro,bromo,andiodo), (2)nitro, (3)nitroso, (4) cyano or isocyano, (5) substituted amino [e.g., a substituted amino of the formula: —NR$^{30}$R$^{31}$ wherein R$^{30}$ and R$^{31}$ each is hydrogen, $C_{1-10}$ alkyl, $C_{3-10}$ cycloalkyl, $C_{2-10}$ alkenyl, $C_{6-14}$ aryl, $C_{7-19}$ aralkyl ($C_{6-14}$ aryl-$C_{1-6}$ alkyl etc.), $C_{1-10}$ acyl ($C_{1-10}$ alkanoyl, preferably $C_{1-4}$ alkanoyl ), $C_{1-6}$ alkoxy-carbonyl, a group of the formula: —S(O)P-R$^{32}$ wherein p represents 1 or 2, and R$^{32}$ represents $C_{1-6}$ alkyl,$C_{1-6}$ alkylsulfonyl, $C_{1-6}$ alkylsulfinyl, or heterocyclic group (the above-mentioned 5- to 8-membered saturated or unsaturated heterocyclic group containing 1 to 4 hetero atoms selected from the group consisting of oxygen, sulfur and nitrogen atoms, or a condensed heterocyclic group thereof); provided that $R^{30}$ and $R^{31}$ are not hydrogen at the same time], (6) hydroxy which may be substituted by (i) $C_{1-6}$ alkyl [this $C_{1-6}$ alkyl may be substituted by halogen, $C_{1-6}$ alkoxy, $C_{2-10}$ alkenyl, $C_{3-10}$ cycloalkyl, $C_{1-3}$ alkylthio, oxy-$C_{1-3}$ alkoxy, $C_{1-6}$ alkyl-carbonyl, carbamoyl, $C_{1-6}$ alkyl-carbamoyl, heterocyclic group (the above-mentioned 5- to 8-membered saturated or unsaturated heterocyclic group containing 1 to 4 hetero atoms selected from the group consisting of oxygen, sulfur and nitrogen atoms, or a condensed heterocyclic group thereof) or halogen], (ii) $C_{1-4}$ acyl, (iii) $C_{7-19}$ aralkyl ($C_{6-14}$ aryl-$C_{1-5}$ alkyl; this $C_{7-19}$ aralkyl may be substituted by halogen, $C_{1-3}$ alkoxy or $C_{1-4}$ alkyl), (iv) $C_{6-14}$ aryl (this $C_{6-14}$ aryl may be substituted by halogen), (v) $C_{2-6}$ alkenyl, (vi) $C_{3-7}$ cycloalkyl, (vii) $C_{1-3}$ alkoxy-carbonyl, (viii) di-$C_{1-6}$ alkylaminocarbonyl, (ix) $C_{1-3}$ alkoxy-carbonyl, (x) $C_{1-6}$ alkylcarbonyl, (xi) $C_{3-6}$ cycloalkyl-oxycarbonyl and (xii) $C_{1-6}$ alkylsulfonyl or $C_{6-14}$ arylsulfonyl each of which may be substituted by halogen, (7) a group of the formula: —S(O) n —$R^{33}$ wherein n represents an integer of 0 to 2, and $R^{33}$ represents hydrogen or a hydrocarbon group which may be substituted by substituent(s) (e.g., halogen, nitro, cyano, oxo, thioxo, cyano-$C_{6-14}$ aryl, halogeno-$C_{6-14}$ aryl etc.); the hydrocarbon group includes $C_{1-20}$ hydrocarbon group, preferably $C_{1-6}$ alkyl, $C_{6-14}$ aryl, $C_{7-19}$ aralkyl ($C_{6-14}$ aryl-$C_{1-6}$ alkyl), (8) carbamoyl which may be substituted (such substituent(s) includes, for example, mono- or di-$C_{1-6}$ alkyl, preferably mono- or di-$C_{1-3}$ alkyl, etc.), (9) a group through carbonyl [e.g., a group of the formula: —CO—$R^{34}$ wherein $R^{34}$ represents (i) hydrogen, (ii) $C_{1-6}$ alkyl, (iii) $C_{1-6}$ alkoxy (this alkoxy may be substituted by $C_{6-14}$ aryl which may be substituted by halogen or nitro, etc.), (v) $C_{3-6}$ cycloalkyl, (vi) $C_{6-14}$ aryl, (vii) $C_{7-19}$ aralkyl ($C_{6-14}$ aryl-$C_{1-6}$ alkyl) or (viii) heterocyclic group (the above-mentioned 5- to 8-membered saturated or unsaturated heterocyclic group containing 1 to 4 hetero atoms selected from the group consisting of oxygen, sulfur and nitrogen atoms, or a condensed heterocyclic group thereof)], (10) heterocyclic group (the above-mentioned 5- to 8-membered saturated or unsaturated heterocyclic group containing 1 to 4 hetero atoms selected from the group consisting of oxygen, sulfur and nitrogen atoms, or a condensed heterocyclic group thereof); this heterocyclic group may be substituted by (i) halogen, (ii) $C_{1-4}$ alkyl, (iii) $C_{1-3}$ alkoxy, (iv) $C_{1-4}$ alkylthio or (v) phenoxy which may be substituted by halogen, (11) $C_{6-14}$ aryl [e.g., phenyl, naphthyl, anthryl, phenanthryl, acenaphthyl, anthracenyl, etc.; this aryl may be substituted by 1 to 4 substituents selected form the group consisting of (a) $C_{1-6}$ alkoxy (e.g., methoxy, ethoxy, propoxy, hexyloxy, etc.), (b) halogen (fluoro, chloro, bromo, and iodo) and (c)di-$C_{1-4}$ alkylamino (e.g., dimethylamino, diethylamino etc.) etc.], (12) $C_{6-14}$ aryloxy [this $C_{6-14}$ aryl is as same as the above (11)], (13) $C_{3-7}$ cycloalkyl, (14) $C_{1-6}$ alkylenedioxy(e.g., methylenedioxy, ethylenedioxy, propylenedioxy, 2,2-dimethylenedioxy etc.), (15) oxo, (16) thioxo, (17) $C_{3-4}$ alkynyl (e.g., propargyl, 2-butynyl, etc.), (18) $C_{3-10}$ cycloalkyl, (19) $C_{2-10}$ alkenyl (e.g., vinyl, allyl, isopropenyl, 1-butenyl, 2-butenyl, butadienyl, hexatrienyl, 3-octenyl etc., preferably $C_{2-6}$ alkenyl), (20) $C_{7-19}$ aralkyl, (21) azido, and so forth.

The substituents of the above-mentioned hydrocarbon group which may be substituted, may further have 1 to 3, preferably 1 or 2 substituents at possible positions. Said substituents, which the substituents may further have, include, for example, 1 to 4, preferably 1 or 2 substituents selected from the group consisting of $C_{1-4}$ alkoxy (e.g., methoxy, ethoxy, propoxy, etc.), halogen (fluoro, chloro, bromo and iodo), nitro and di-$C_{1-4}$ alkylamino (e.g., dimethylamino, diethylamino, etc.), etc.

When the hydrocarbon group is cycloalkyl, alkenyl, alkynyl, cycloalkenyl, aryl or aralkyl, this hydrocarbon group maybe substituted 1 to 3 $C_{1-6}$ alkyl (e.g., methyl, ethyl, propyl, isopropyl, butyl, etc.), and this $C_{1-6}$ alkyl may be further substituted by 1 to 3 oxo, $C_{1,3}$ alkoxy (e.g., methoxy, ethoxy, ethoxy, n-propoxy, isopropoxy etc.) $C_{1-3}$ alkylthio, halogen, and carbamoyl, etc.

The substituted $C_{1-6}$ alkyl includes, formyl (methyl substituted by an oxo), $C_{1-6}$ alkoxycarbonyl (methyl substituted by an oxo and an alkoxy) (e.g., $C_{1-6}$ alkoxycarbonyl such as methoxycarbonyl, ethoxycarbonyl, t-butoxycarbonyl, etc.), $C_{1-3}$ alkoxy-$C_{1-6}$ alkyl (e.g., methoxymethyl, ethoxymethyl, ethoxybutyl, propoxymethyl, propoxyhexyl, etc.), and so forth.

The number of the above substituents is 1 to 6, preferably 1 to 5, more preferably 1 to 3, especially 1 or 2. The number of the substituents which substituents may further have, is 1 to 3, preferably 1 to 2.

In the definitions of the above-mentioned groups, $C_{1-10}$ alkyl includes, for example, methyl, ethyl,-propyl, isopropyl, butyl, isobutyl, sec-butyl, t-butyl, pentyl, isopentyl, neopentyl, hexyl, etc., preferably $C_{1-6}$ alkyl, more preferably $C_{1-4}$ alkyl or $C_{1-3}$ alkyl. The $C_{1-6}$ alkyl includes, for example, methyl, ethyl, n-propyl, isopropyl, n-butyl, isobutyl, sec-butyl, t-butyl, pentyl, isopentyl, neopentyl, hexyl,etc. The $C_{1-4}$ alkyl includes,for example,methyl,ethyl, n-propyl. isopropyl, n-butyl, isobutyl, sec-butyl, and t-butyl. The $C_{1-3}$ alkyl includes, for example, methyl, ethyl, n-propyl, and isopropyl.

In the definitions of the above-mentioned groups, $C_{3-10}$ cycloalkyl includes, for example, cyclopropyl, cyclobutyl, cyclopentyl, cyclohexyl, cycloheptyl, cyclooctyl, cyclononyl, etc., preferably $C_{3-7}$ cycloalkyl (e.g., cyclopropyl, cyclobutyl, cyclopentyl, cyclohexyl, cycloheptyl, etc.), more preferably $C_{3-6}$ cycloalkyl (e.g., cyclopropyl, cyclobutyl, cyclopentyl, cyclohexyl, etc.).

In the definitions of the above-mentioned groups, $C_{2-10}$ alkenyl includes, for example, vinyl, allyl, 1-butenyl, 2-butenyl, butadienyl, isopropenyl, 2-methylallyl hexatrienyl, 3-octenyl, etc., preferably $C_2$-alkenyl (e.g., vinyl, allyl, 1-butenyl, 2-butenyl, butadienyl, isopropenyl, 2-methylallyl, hexatrienyl, etc.).

In the definitions of the above-mentioned groups, $C_{6-14}$ aryl includes, for example, phenyl, naphthyl, anthryl, phenanthryl, acenaphthyl, anthracenyl, etc. Preferred is $C_{6-10}$ aryl.

In the definitions of the above-mentioned groups, $C_{7-19}$ aralkyl includes, for example, benyl, phenethyl, benzhydryl, trityl, etc.

In the definitions of the above-mentioned groups, $C_{1-6}$ alkoxy includes, for example, methoxy, ethoxy, n-propoxy, isopropoxy, n-butoxy, isobutoxy, sec-butoxy-butoxy, etc.

Among others preferred is $C_{1-4}$ alkoxy or $C_{1-3}$ alkoxy (e.g., methoxy, ethoxy, n-propoxy, and isopropoxy).

In the definitions of the above-mentioned groups, $C_{1-10}$ acyl includes, for example, $C_{1-10}$ alkanoyl (e.g., formyl, acetyl, propionyl, butyryl, isobutyryl, valeryl, hexanoyl), etc. Among others, preferred is $C_{1-4}$ acyl [e.g., $C_{1-4}$ alkanoyl (e.g., formyl, acetyl, propionyl, butyryl, isobutyryl etc.].

Preferred examples of the substituents of the hydrocarbon group which may be substituted for $R^1$ include (1) nitro, (2) amino which may be substituted by $C_{1-10}$alkyl, $C_{1-10}$ acyl ($C_{1-10}$ alkanoyl) or $C_{1-6}$ alkoxy-carbonyl, (3) hydroxy which may be substituted by $C_{1-6}$ alkyl, $C_{1-4}$ acyl ($C_{1-4}$ alkanoyl), $C_{1-30}$ alkoxy-carbonyl, $C_{1-6}$ alkylcarbonyl, $C_{1-6}$ cycloalkyl-oxycarbonyl or trifluorosulfonyl, (4) a group of the formula: —S(O) n —$R^{12}$ wherein n represents an integer of 0 to 2, and $R^{12}$ represents hydrogen or $C_{1-20}$ hydrocarbon group (preferably $C_{1-6}$ alkyl), and so forth.

$R^1$ is preferably (1) $C_{1-20}$ hydrocarbon group (preferably $C_{1-6}$ alkyl) and (2) $C_{1-20}$ hydrocarbon group (preferably $C_{1-6}$ alkyl) substituted by amino which may be substituted by $C_{1-6}$ alkyl, $C_{7-19}$ aralkyl ($C_{6-14}$ aryl-$C_{1-6}$ alkyl), etc. More preferably $R^1$ is (1) $C_{1-6}$ alkyl and (2) N—$C_{7-19}$ aralkyl-N—$C_{1-6}$ alkylamino-$C_{1-6}$ alkyl (N—$C_{6-14}$ aryl-$C_{1-5}$ alkyl-N—$C_{1-6}$ alkylamino-$C_{1-6}$ alkyl) etc.

Preferred examples of the substituents of the hydrocarbon group which may be substituted for $R^2$ include (1) nitro, (2) halogen, (3) a group of the formula: —S(O) n —$R^{12}$ wherein n represents an integer of 0 to 2, and $R^{12}$ represents hydrogen or $C_{1-20}$ hydrocarbon group (preferably $C_{1-6}$ alkyl), (4) carbamoyl, (5) a group through carbonyl (e.g., $C_{1-6}$ alkoxy-carbonyl, etc.), and so forth.

$R^2$ is preferably $C_{1-20}$ hydrocarbon group (e.g., $C_{6-14}$ aryl). More preferably $R^2$ is (1) $C_{6-14}$ aryl, (2) $C_{1-8}$ alkanoyl-amino-$C_{6-14}$ aryl, (3) $C_{2-10}$ alkenyl-$C_{1-6}$ alkoxy-$C_{6-14}$ aryl, and so forth.

In the formulae, the halogen for X includes fluoro, chloro, bromo and iodo. Among others, preferred is bromo.

$R^3$ is preferably $C_{1-20}$ hydrocarbon group (e.g., $C_{1-6}$ alkyl, $C_{2-6}$ alkenyl, $C_{6-14}$ aryl, etc.). More preferred is methyl, isopropyl or phenyl.

$R^4$ is preferably $C_{1-20}$ hydrocarbon group (e.g., $C_{1-6}$ alkyl, $C_{2-6}$ alkenyl, $C_{6-14}$ aryl, etc.). More preferred is ethyl, etc.

$R^5$ is preferably hydrogen.

$R^6$ represents hydrogen, sodium, potassium or a hydrocarbon group. $R^6$ is preferably $C_{1-20}$ hydrocarbon group (e.g., $C_{1-6}$ alkyl, $C_{2-6}$ alkenyl, $C_{6-14}$ aryl, etc.).

The production of the present invention is as follows.

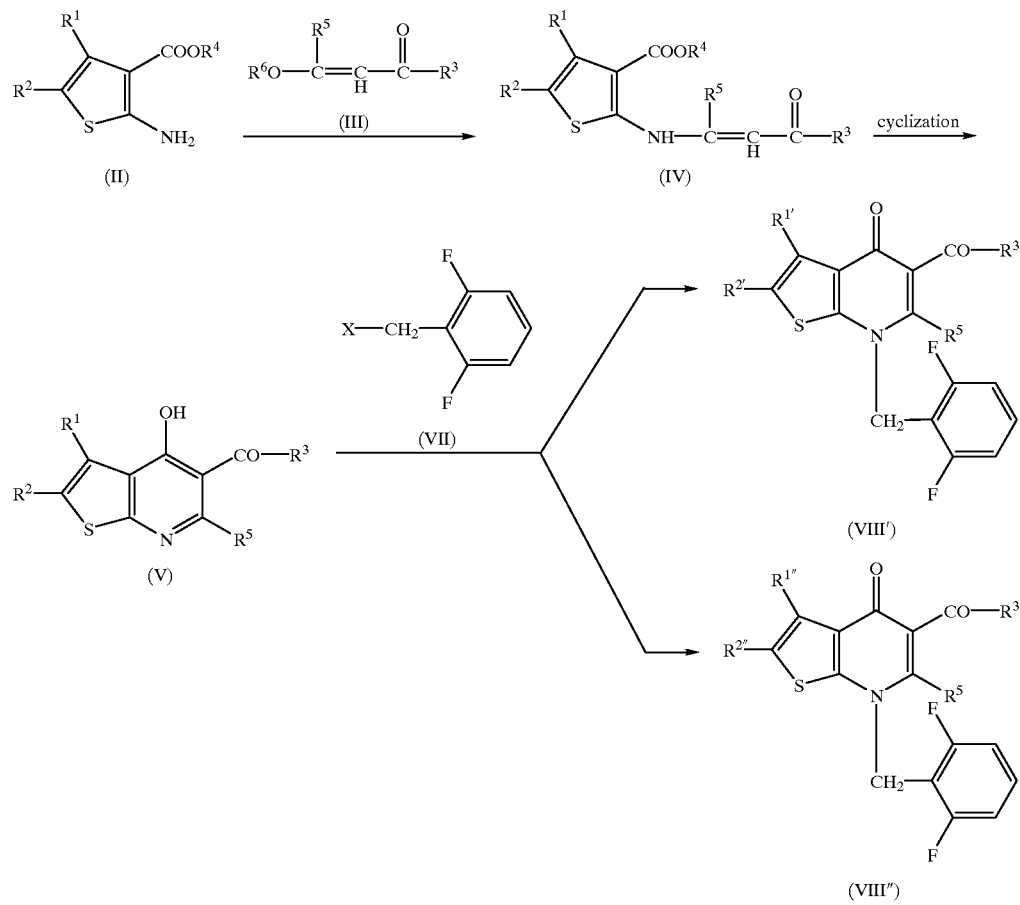

wherein $R^{1'}$ and $R^{2'}$ each represents a hydrocarbon group which may be substituted, $R^{1''}$ and $R^{2''}$ form, taken together with adjacent two carbon atoms, a 5- to 7-membered ring which may be substituted, and other symbols are as defined above.

The above "hydrocarbon group which may be substituted" and the "5- to 7-membered ring which may be substituted" are as defined above, respectively. The compound of the above formula (VIII') is sometimes refereed as compound (VIII'). The compound of the above formula (VIII") is sometimes refereed as compound (VIII").

1. Cyclization is Carried Out as Follows.

(1) Firstly, thiophene compound (II) is reacted with compound (III) to produce compound (IV).

In this reaction, about 1 to 5 mol, preferably 1 to 2 mol of compound (III) is used relative to one mol of compound (II).

In this reaction, there is no particular limitation on the kind of solvent that can be used unless the reaction is interfered with. Such solvent includes, for example, hydrocarbons (e.g., n-hexane, benzene, toluene, xyxlene, etc.), halogenated hydrocarbons (e.g., dichloromethane, 1,2-dichloroethane, chloroform, carbon tetrachloride, etc.), ethers (e.g., diethylether, diisopropylether, ethylene glycol dimethyl ether, tetrahydrofuran, dioxane, etc.), nitrites (e.g., acetonitrile, etc.), esters (e.g., ethyl acetate, etc.), amides (e.g., N,N-dimethylformamide, etc.), ketones (e.g., acetone, methyl ethyl ketone, etc.), sulfoxides (e.g., dimethylsulfoxide, etc.) and mixtures of those solvents. This reaction is preferably carried out in the presence of an acid to promote this reaction. The acid includes an inorganic acid such as hydrochloric acid, hydrobromic acid, sulfuric acid and phosphoric acid, an organic acid such as acetic acid, trifluoroacetic acid, methanesulfonic acid, benzenesulfonic acid and p-toluenesulfonic acid. The amount of the acid is about 0 to 5 equivalents, preferably about 0.01 to 0.5 equivalents relative to one mol of compound (II).

The reaction temperature is about 0 to 180° C., preferably about 10 to 50° C. The reaction time is about 10 minutes to 24 hours, preferably about 1 to 2 hours.

Compound (II) is produced by the per se known method, for example, the method described in K. Gewald, et. al., Chem. Ber. 99, 94, 1966, or analogue methods thereto. Compound (III) is produced by the per se known method, for example, methods described in J. Dabrowski, et. al., Bull. Chem. Soc. Jpn. 48 1310, 1975, or U. Lienhard, et. al., Helv. Chim. Acta, 61, 1609, 1978, or analogous methods thereto.

(2) The reaction in which compound (IV) is subjected to cyclization to produce compound (V) is carried out by heating compound (IV).

The reaction is carried out by heating compound (IV) at about 100 to 300° C., preferably about 200 to 280° C., for about 30 minutes to 30 hours, preferably about 1 to 6 hours, with distilling off an alcohol (e.g., ethanol, etc.) which is produced during the reaction.

This reaction may be carried out without a solvent or in the presence of a solvent. When a solvent is used, preferred is a solvent which does not interfere with the cyclization and has a high boiling point (e.g., a solvent having b.p. 100° C. or more). Such solvent includes, for example, diethylene glycol dibutyl ether, diphenyl ether, diethyl phthalate, etc.

2. A Compound of the Formula:

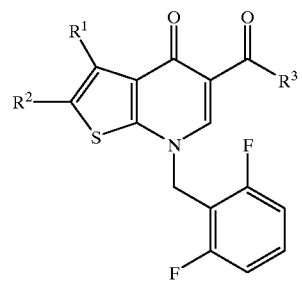

wherein each symbol is as defined above, can be produced [hereinafter, sometimes referred to as compound (VIII)] by introducing a difluorophenyl-methyl group to the 7-position of compound (V).

In this reaction about 1 to 2 mol. preferably about 1 to 1.2 mol of halogenated difluorophenyl-methyl compound is added relative to one mol of compound (V).

This reaction is advantageously carried out in the presence of a base. Such base includes, for example, an inorganic base such as an alkali metal or alkaline earth metal hydrogencarbonate (e.g., sodium hydrogencarbonate, potassium hydrogencarbonate, etc.), an alkali metal or alkaline earth metal carbonate (e.g., sodium carbonate, potassium carbonate, etc.), an alkali metal or alkaline earth metal hydroxide (e.g. sodium hydroxide, potassium hydroxide, calcium hydroxide, etc.) and an organic base such as an alkylamine (e.g., triethylamine, diisopropylethylamine, etc.), and so forth. The amount of the base to be used is about 1 to 2 mol relative to one mol of compound (V).

In this reaction, there is no particular limitation on the kind of solvent that can be used unless the reaction is interfered with. Among others, preferred are ethers (e.g., diethyl ether, diisopropyl ether, ethylene glycol dimethyl ether, tetrahydrofuran, dioxane, etc.), nitrites (e.g., acetonitrile, etc.), amides (e.g., N,N-dimethylformamide etc.), ketones (e.g., acetone, methyl ethylketone, etc.), etc.

The reaction temperature is about 0 to 100° C., preferably about 20 to 50° C. The reaction time is about 1 to 24 hours, preferably about 2 to 3 hours.

Salts of compounds used in these reactions and salts of compounds obtained in these reactions (hereinafter, referred to as "compound of the present invention") are preferably physiologically acceptable acid addition salts. Such salts include, for example, salts with inorganic acids (e.g., hydrochloric acid, phosphoric acid hydrobromic acid, sulfuric acid, etc.), saltswithorganic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), and so forth. For example, when a compound of the present invention has an acidic group such as carboxylic acid, it may form a physiologically acceptable salt with an inorganic base (e.g., alkali metals or alkaline earth metals such as sodium, potassium, calcium and magnesium; ammonia; etc.) or an organic base (e.g., tri-$C_{1-3}$ alkylamine such as triethylamine, etc.). The compound in free form can be converted to a salt and the one in salt form can be converted to a free form by per se known methods or analogous thereto.

In JP-A-8-295693 (WO 95/28405), 2-(4-aminophenyl)-3-(N-benzyl-N-methylaminomethyl)-7-(2,6-difluorobenzyl)-4,7-dihydro-5-isobutyryl-4-oxothieno[2,3-b]pyridine is shown merely as an amorphous. In the present invention, 2-(4-aminophenyl)-3-(N-benzyl-N-methylaminomethyl)-7-(2,6-difluorobenzyl)-4,7-dihydro-5-isobutyryl-4-oxothieno[2,3-b]pyridine can be obtained as a stable crystalline salt according to, for example, the following examples. The above crystalline salts include physiologically acceptable acid addition salts such as salts with inorganic acids (e.g., hydrochloric acid, phosphoric acid, hydrobromic acid, sulfuric acid, etc.), salts withorganic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), and so forth. Preferably, the crystalline salts are salts with hydrochloric acid, methanesulfonic acid, dibasic acid (e.g., fumaric acid, oxalic acid, malonic acid, succinic acid, malic acid, etc.), or tribasic acid (e.g., 1,2,3-propanetricarboxylic acid, etc.), more preferably, salts with dibasic acid (preferably, fumaric acid, malonic acid, succinic acid, malic acid, etc.).

Crystalline salt of 2-(4-aminophenyl)-3-(N-benzyl-N-methylaminomethyl)-7-(2,6-difluorobenzyl)-4,7-dihydro-5-isobutyryl-4-oxothieno[2,3-b]pyridine, of the present invention is stable so that it can be easily isolated and purified and it can be preserved in stable condition for long term.

When the compound has a double bond, and there exist stereoisomers of Z- or E-form, Z-form, E-form and their mixture may be used.

When the compound has a chiral carbon atom, and there exist stereoisomers, each of them and their mixture are within the scope of the present invention.

When the compound of the present invention or a salt thereof is an optically active compound, it can be resolved into the d- and l -forms by the conventional optical resolution techniques.

Thus obtained compound or its salt may be isolated and purified by ordinary means of separation such as solvent extraction, concentration under reduced pressure, crystallization, recrystallization, distillation chromatography, and the like.

The compound obtained in the present invention or a salt thereof can be submitted to the next reaction either as the reaction mixture or after partial purification.

Compound (VIII) obtained by the methods of the present invention or a salt thereof can be used as a synthetic intermediate for production of thienopyridine derivatives having GnRH antagonistic activity or compounds containing such derivative as partial structure [hereinafter, sometimes referred to as compound (IX)].

Thienopyridine derivatives having GnRH antagonistic activity [hereinafter, referred to as compound (IX')] or their salts can be produced from thienopyridine derivatives in compound (VIII) [hereinafter, referred to as compound (VIII')] or their salts, according to methods described in JP-A-8-295693 (WO 95/28405) or analogous methods thereto.

Since a compound of Formula (VIII) wherein a ring formed by $R^{10}$ and $R^2$ together with adjacent two carbon atoms has a substituent [hereinafter, referred to as compound (VIII")] or its salt can be used in a manner similar to that described in JP-A-8-295693 (WO 95/28405) by converting the substituent in said compound or by further introducing a substituent thereinto to produce a GnRH antagonistic compound [sometimes abbreviated as compound (IX"), which means a compound having as a part a thienopyridine derivative described above] or its salt, compound (VIII") or its salt can be used as an intermediate for producing compound (IX") or its salt.

Since compound (IX) or its salt has a GnRH antagonistic activity with a low toxicity, it can be used as a GnRH antagonist in a manner similar to that described in JP-A-8-295693 (WO 95/28405).

A thienopyridine derivative described above (compound (IX) or its salt) produced from a compound obtained by a method of the invention has an excellent GnRH antagonistic activity and has a low toxicity. Accordingly, said thienopyridine derivative suppresses the secretion of a gonadotropin through its GnRH receptor antagonism in a mammal (for example, human, monkey, cattle, horse, dog, cat, rabbit, rat, mouse, etc.) to provide a control of the blood levels of sex hormones, due to which it can safely be employed in the prophylaxis and the treatment of a androgenic hormone- or estrogenic hormone-dependent disease or a disease attributable to the hypersecretion of such hormone.

For example, said thienopyridine derivative is useful in the prophylaxis and the treatment of a sex hormone-dependent cancer (e.g., prostatic cancer, uterine cancer, mammary cancer, pituitary tumor, etc.) as well as prostatomegaly, hysteromyoma, endometriosis, precocious puberty, amenorrhea, premenstrual syndrome, multilocular ovary syndrome, acne and the like. It is useful also in the preoperative treatment before a surgery of any disease listed above as well as in the postoperative prevention of a recurrence. Said thienopyridine derivative is useful also in controlling the reproduction in males and females (e.g., pregnancy regulator, menstrual period regulator, etc.). A thienopyridine derivative may be used also as a contraceptive in males and females or as an ovulation-promoting agent in females. Said thienopyridine derivative may be used in the treatment of a sterility by utilizing the rebound effect thereof after discontinuation.

Said thienopyridine derivative of the invention is useful also in a field of stockbreeding for controlling an estrus of an animal, improving the texture of a meat, or promoting the growth of an animal. Said thienopyridine derivative is useful also as a opposition-promoting agent in fish.

The following examples merely illustrate this invention in further detail and should by no means be construed as defining the scope of the invention.

EXAMPLE 1

Production of 3-Bromomethyl-7-(2,6-difluorobenzyl)-4,7-dihydro-4-oxo-2-phenylthieno[2,3-b]pyridine-5-carboxylic Acid Ethyl Ester 7-(2,6-difluorobenzyl-4,7-dihydro-3-methyl-4-oxo-2-phenylthieno[2,3-b]pyridine-5-carboxylic acid ethyl ester obtained as in Example 3(13) in WO 95/28405 (JP-A-8-295693) (1200 g), N-bromosuccinimide (589 g), 2,2'-azobisisobutylonitrile (AIBN) (45.3 g) were suspended in ethyl acetate (13.3 L) and the mixture was stirred under reflux for 2.5 hours. After dissolving once, a crystal of the title compound was precipitated slowly. The mixture was allowed to cool with stirring, and then cooled with water and then on ice. The crystal was recovered by a filtration, washed with ethyl acetate (1 L) (twice) and a purified water (2.7 L)(twice) and then dried at 50° C. for 9 hours to obtain 1295 g of the title compound,(yield: 92%).

m.p. 206–206° C.

EXAMPLE 2

Production of 3-Bromomethyl-7-(2,6-difluorobenzyl)-4,7-dihydro-2-(4-nitrophenyl)-4-oxothieno[2,3-b]pyridine-5-carboxylic Acid Ethyl Ester To methanesulfonic acid (4.5 L), 900 g of the compound obtained in Example 1 described above was added over a period of 30 minutes (internal temperature 19 to 23° C.). After cooling on ice with stirring, sodium nitrate (147 g)/methanesulfonic acid (1.98 L) was added dropwise over a period of 2 hours (internal temperature 12 to 14° C.). Subsequently, the reaction mixture was stirred for 1.5 hours at 11 to 12° C., and was added to 155 L of an ice-water, and the precipitated crystal was recovered by a filtration, washed with water and then dried. 1The crystal was dried in vacuo for 26 hours at 50° C. to obtain 944 g of a crude product of the title compound (yield: 75%, HPLC). The crystal was suspended in ethyl acetate (2.9 L), and the mixture was stirred under reflux for 30 minutes, at room temperature for 30 minutes, and then stirred with cooling on ice for 1 hour and 20 minutes. The crystal was recovered by a filtration, washed with cool ethyl acetate (0.8 L), dried under reduced pressure for 8 hours at 50° C. to obtain 837 g of the title compound (yield: 86%).

m.p. 200–202° C.

EXAMPLE 3

Production of 3-(N-Benzyl-N-methylaminomethyl)-7-(2,6-difluorobenzyl)-4,7-dihydro-2-(4-isobutyrylaminophenyl)-4-oxothieno[2,3-b]pyridine-5-carboxylic Acid (1) The compound obtained in Example 2 described above was subjected to the process described in Example 26(2) in WO 95/28405 (JP-A-8-295693) and the process described in Example 27(2) in the same reference to obtain 2-(4-aminophenyl)-3-(N-benzyl-N-methylaminomethyl)-7-(2,6-difluorobenzyl)-4,7-dihydro-4-oxothieno[2,3-b]pyridine-5-carboxylic acid ethyl ester.

(2) The compound obtained in the above step (1) was admixed with a slightly excess of isobutyrylchloride in pyridine and stirred at room temperature for 2 hours to obtain 3-(N-benzyl-N-methylaminomethyl)-7-(2,6-difluorobenzyl)-4,7-dihydro-2-(4-isobutyrylaminophenyl)-4-oxothieno[2,3-b]pyridine-5-carboxylic acid ethyl ester.

m.p. 185-186° C.

(3) The compound (735 g) obtained in the above step (2) was dissolved in ethanol (11 L) and combined with 2.5 N NaOH (4.57 L), and stirred for 3 hours at an internal temperature of 40±5° C. After distilling ethanol off under reduced pressure, the residue was combined with water (7.4 L) and adjusted with concentrated hydrochloric acid (989 ml) to pH 5.4. After extraction with 2-butanone (14.5 L, 7.4 L; twice), the organic phase was washed with saturated saline and then concentrated under reduced pressure. While suspended in 2-butanone (1.6 L) with stirring, isopropylether (3.3 L) was added dropwise. After cooling on ice and then recovering by filtration, washing was performed with diisopropylether. After drying in air and drying at 50° C. for 9 hours under reduced pressure, 605 g of the title compound (yield: 93%) was obtained.

NMR (CDCl$_3$, δ): 1.27(d, 6H, J=6.8 Hz), 2.20(s,3H), 2.63(m,1H), 3.75(s,2H), 4.20(s,2H), 5.41(s,2H), 6.9–7.7(m, 12H), 8.69(s,1H).

EXAMPLE 4

Production of 3-(N-Benzyl-N-methylaminomethyl)-7-(2,6-difluorobenzyl)-4,7-dihydro-2-(4-isobutyrylaminophenyl)-4-oxothieno[2,3-b]pyridine-5-(N-methyl-O-methyl)hydroxamic Acid A mixture of the compound obtained in Example 3 described above (574 g), acetonitrile (4.6 L), N,O-dimethylhydroxylamine hydrochloride (182 g), triethylamine (261 ml), hydroxybenzotriazole (HOBT) (253 g) and 1-( 3-dimetylaminopropyl)-3-ethylcarbodilmide hydrochloride (WSC) (179 g) was stirred with heating at 50 to 59° C. WSC (250 g) was further added in 4 portions. Acetonitrile was distilled off under reduced pressure, and the residue was combined with 2-butanone (12 L) and saturated saline (8 L) and the mixture was stirred vigorously. After separating the organic phase, the aqueous phase was extracted with 2-butanone. The organic phases were combined and washed twice with saturated saline (5.6 L). After dryiny over magnesium sulfate followed by distilling the solvent off under reduced pressure, ethyl acetate was added and then concentrated again under reduced pressure. After concentrating to about 1.6 L followed by cooling on ice, the precipitated crystal was recovered by a filtration. Then, after washing with cool ethyl acetate (640 ml) followed by drying at 50° C. under reduced pressure for 9 hours, 556 g of the title compound (yield: 91%) was obtained.

m.p. 152–154° C.

EXAMPLE 5

Production of 3-(N-Benzyl-N-methylaminomethyl)-7-(2,6-difluorobenzyl)-4,7-dihydro-2-(4-isobutyrylaminophenyl)-5-isobutyryl-4-oxothieno[2,3-b]pyridine Hydrochloride The compound obtained in the above Example 4 is subjected to the procedure described in Reference 18 in JP-A-9-169766 to obtain the title compound.

EXAMPLE 6

Production of 7-(2,6-Difluorobenzyl)-4,7-dihydro-3-methyl-4-oxo-2-phenylthieno[2,3-b]pyridine-5-carboxylic Acid 7-(2,6-Difluorobenzyl-4,7-dihydro-3-methyl-4-oxo-2-phenylthieno[2,3-b]pyridine-5-carboxylic acid ethyl ester obtained as in Example 3(13) in WO 95/28405 (JP-A-8-295693)(200.0 g) was dissolved in ethanol (3.0 L) and combined with 8 N NaOH (170.7 ml), and stirred with heating under reflux for 1 hour. After distilling ethanol of under reduced pressure, the residue was combined with water (2 L) and the pH was then adjusted to 5 with concentrated hydrochloric acid (117 ml). The crystal precipitated was recovered by a filtration, washed with water, dried in air and then at 50° C. under reduced pressure for 9 hours to obtain 184.6 g of the title compound (yield: 98.6%).

m.p. 286–289° C.

EXAMPLE 7

Production of 7-(2,6-Difluorobenzyl)-4,7-dihydro-3-methyl-4-oxo-2-phenylthieno[2,3-b]pyridine-5-(N-methyl-O-methyl)hydroxamic Acid The compound obtained in the procedure of the above Example 6 (1.0 g) was dissolved in a dried tetrahydrofuran (THF) and the reaction vessel was purged with an argon gas. While stirring with cooling on ice, thionyl chloride (0.24 ml) was added and the mixture was stirred at room temperature for 4 hours and then concentrated to dryness under reduced pressure to obtain 7-(2,6-difluorobenzyl)-4,7-dihydro-3-methyl-4-oxo-2-phenylthio[2,3-b]pyridine-5-carboxylic acid chloride as a residue, which was then dissolved in a dried THF.

A mixture of N,O-dimethylhydroxylamine (0.30 g), triethylamine (0.34 ml) and a dried THF was stirred with cooling on ice, and treated dropwise with the solution of the acid chloride described above in a dried THF. To the reaction mixture, chloroform (40 ml) and water (30 ml) were added and the mixture was stirred vigorously and then the organic phase was separated. The organic phase was washed with saturated saline (30 ml) and dried over magnesium sulfate, and the solvent was distilled off under reduced pressure. To the residue, 2-butanone (3 ml) and diisopropylether (6 ml) were added, and after allowing a crystal to be precipitated, the mixture was stirred with cooling on ice. The crystal was recovered by a filtration, and washed with diisopropyl ether. After drying at 40° C. under reduced pressure for 6 hours, 1.07 g of the title compound was obtained (yield: 97%).

m.p. 247–250° C.

EXAMPLE 8

Production of 7-(2,6-Difluorobenzyl)-4,7-dihydro-5-isobutyryl-3-methyl-4-oxo-2-phenylthieno[2,3-b] pyridine Using the compound obtained in Example 7, the title compound was obtained in the manner similar to that in Example 5.

m.p. 204–207° C.

EXAMPLE 9

Production of 3-Byomomethyl-7-(2,6-difluorobenzyl)-4,7-dihydro-5-isobutyryl-4-oxo-2-phenylthieno[2,3-b]pyridine Using the compound obtained in the above Example 8, the title compound was obtained in the manner similar to that in the above Example 1.

m.p. 189–192° C.

EXAMPLE 10

Production of 3-Bromomethyl-7-(2,6-difluorobenzyl)-4,7-dihydro-5-isobutyryl-2-(4-nitrophenyl)-4-oxothieno[2,3-b]pyridine Using the compound obtained in the above Example 9, the title compound was obtained in the manner similar to that in Example 2.

m.p. 202–204° C.

EXAMPLE 11

Production of 3-(N-Benzyl-N-methylaminomethyl)-7-(2,6-difluorobenzyl)-4,7-dihydro-5-isobutyryl-2-(4-isobutyrylaminophenyl)-4-oxothieno[2,3-b] pyridine Hydrochloride The compound obtained in the above Example 10 is subjected to the method-in Example 47(2) in WO 95/28405 (JP-A-8-295693) followed by the method in Example 55 in the same reference, and further followed by the method in Example 57(10) in the same reference to obtain the title compound.

The chemical structure of the compounds obtained in Examples 1, 2, 4 and 7 to 10 are shown in Table 1.

TABLE 1

| Ex. No. | $R^{1a}$ | $R^{2a}$ | $R^{45a}$ |
|---|---|---|---|
| 1 | bromomethyl | phenyl | ethoxycarbonyl |
| 2 | bromomethyl | 4-nitrophenyl | ethoxycarbonyl |
| 4 | N-benzyl-N-methylaminomethyl | 4-isobutyrylaminophenyl | (N-methyl-O-methyl)-hydroxamic acid |
| 7 | methyl | phenyl | (N-methyl-O-methyl)-hydroxamic acid |
| 8 | methyl | phenyl | isopropyl |
| 9 | bromomethyl | phenyl | isopropyl |
| 10 | bromomethyl | 4-nitrophenyl | isopropyl |

EXAMPLE 12

Production of 2-Amino-5-(4-isobutyrylaminophenyl)-4-methylthiophene-3-carboxylic Acid Ethyl Ester 4-Isobutyrylaminophenylacetone (5 g), ethyl cyanoacetate (3.09 g), ammonium acetate (0.53 g) and acetic acid (30 ml) were admixed and heated under reflux for 4 hours. After distilling acetic acid off under reduced pressure, the residue was partitioned between ethyl acetate (50 ml) and a 5% aqueous solution of sodium hydrogencarbonate (50 ml). The organic phase was washed with a 5% aqueous solution of sodium hydrogen carbonate (50 ml) and a 5% saline (50 ml), and the solvent was distilled off under reduced pressure, and the residue was heated azeotropically with ethyl acetate (10 ml) and ethanol (10 ml). The residue was dissolved in ethanol (43 ml) and combined with diethylamine (1.67 g) and sulfur (0.73 g), and the mixture was stirred at room temperature for 3 hours. The reaction mixture was partitioned between ethyl acetate (100 ml) and a 5% saline (50 ml), and then the organic phase was washed successively with a 5% saline (50 ml), a 5% aqueous solution of sodium hydrogen carbonate (50 ml) and then a 5% saline (50 ml). The solvent was distilled off under reduced pressure to obtain a residue, which was subjected to a column chromatography on a silica gel (ethyl acetate/hexane=7/3) followed by a recrystallization from diisopropylether/hexane=1/1 (100 ml) to obtain the title compound (4.85 g).

$^1$HNMR(300 MHz,CDCl$_3$)δ; 1.27(d,6H,J=6.9 Hz), 1.37 (t,3H,J=7.1 Hz), 2.30(s,3H), 2.52(sept,1H,J=6.9 Hz), 4.31 (q,2H,J=7.1 Hz), 6.08(bs,2H), 7.18(bs,1H), 7.29(d,2H,J=8.5 Hz), 7.54(d,2H,J=8.5 Hz).

EXAMPLE 13

Production of 4-Methyl-2-[(4-methyl-3-oxo-1-penten-1-yl)amino]-5-phenylthiophene-3-carboxylic Acid Ethyl Ester 2-Amino-4-methyl-5-phenylthiophene-3-carboxylic acid ethyl ester [m.p. 93–95° C., a compound obtained by a method similar to that described in WO 95/28405 (JP-A-8-295693), hereinafter the same is applied analogously.] (10 g), a 85% pure of 1-methoxy-4-methyl-1-penten-3-one (6.9 g), p-toluenesulfonic acid monohydrate (0.219 g) and toluene (100 ml) were mixed and the mixture was stirred at room temperature for 2.5 hours. The reaction mixture was diluted with ethyl acetate and washed with a saturated aqueous solution of sodium hydrogen carbonate and the aqueous layer (wash) was extracted with ethyl acetate. The organic phases were combined and washed with a saturated saline, and then dried over anhydrous magnesium sulfate. The residue (precipitate) was triturated with hexane and the filter cake was washed with hexane to obtain the title compound (12.64 g, 92.4%).

m.p. 104–108° C.

EXAMPLE 14

Production of 4-Hydroxy-5-isobutyryl-3-methyl-2-phenylthieno[2,3-b]pyridine

The compound obtained in Example 13 (50 g) and diphenylether (500 ml) were mixed and the ethanol formed as the reaction proceeded was distilled off while continuing the heating under reflux for 4 hours. After allowing to cool followed by distilling diphenylether off under reduced pressure a crude crystal was precipitated and washed with n-hexane to obtain the title compound (35.1 g, 80.6%).

m.p. 114–117° C.

EXAMPLE 15

Production of 7-(2,6-Difluorobenzyl)-4,7-dihydro-5-isobutyryl-3-methyl-4-oxo-2-phenylthieno[2,3-b]pyridine The compound obtained in Example 14 (35 g), potassium carbonate (18.6 g) and N,N-dimethylformamide (280 ml) were mixed, and 2,6-difluorobenzyl bromide (27.9 g) was added, and the mixture was stirred at room temperature for 4 hours. Water (560 ml) was added dropwise to the reaction mixture, and the mixture was stirred for 30 minutes,-cooled on ice, and then stirred further for 1 hour. The crude crystal was recovered by a filtration, washed with water, dried in air, and then suspended in a 1:1 solvent mixture (250 ml) of ethyl acetate and diisopropylether, and the suspension was stirred at 25 to 40° C. for 1 hour, and then stirred with cooling on ice for 1 hour, and the crystal precipitated out was recovered by a filtration and washed with the solvent mixture described above (125 ml) to obtain the title compound (44.6 g, 91.7%).

m.p. 205–207° C.

EXAMPLE 16

Production of 3-Bromomethyl-7-(2,6-difluorobenzyl)-4,7-dihydro-5-isobutyryl-4-oxo-2-phenylthieno[2,3-b]pyridine The compound obtained in Example 15 (1.8 g) was admixed with N-bromosuccinimide (0.88 g), azobisisobutyronitrile (70 mg) and ethyl acetate (18 ml) and the mixture was heated under reflux for 2 hours. At the time when about 1 hour and 30 minutes had elapsed during this procedure, the suspension turned into a solution. The suspension obtained after allowing to cool was cooled on ice, and the precipitated crystal was recovered by a filtration, washed with cool ethyl acetate and water to obtain the title compound (1.68 g, 79.1%).

m.p. 189–192° C.

EXAMPLE 17

Production of 3-Bromomethyl-7-(2,6-difluorobenzyl)-4,7-dihydro-5-isobutyryl-2-(4-nitrophenyl)-4-oxothieno[2,3-b]pyridine The compound obtained in Example 16 (1 g) was dissolved in methanesulfonic acid (5 ml) with cooling at 10 to 12° C. and then treated dropwise with a solution of sodium nitrate (0.165 g) in methanesulfonic acid (2.5 ml). The mixture was stirred as it was for 2 hours, and then poured into a cool water, and the crystal precipitated was recovered by a filtration, washed with water and diisopropylether, dried in vacuo to obtain a crude crystal (1.04 g). This was suspended in ethyl acetate (15 ml) with stirring and then cooled on ice, and the crystal precipitated was recovered by a filtration, washed with a cool ethyl acetate to obtain the title compound (0.647 g, 59.5%).

m.p. 202–204° C. (recrystallized from methanol).

EXAMPLE 18

Production of 3-(N-Benzyl-N-methylaminomethyl)-7-(2,6-difluorobenzyl)-4,7-dihydro-5-isobutyryl-2-(4-isobutyrylaminophenyl)-4-oxothieno[2,3-b] pyridine Hydrochloride The compound obtained in the above Example 17 is subjected to the method in Example 47(2) in WO 95/28405 (JP-A-8-295693) followed by the method in Example 55 in the same reference, and further followed by the method in Example 57(10) in the same reference to obtain the title compound.

EXAMPLE 19

Production of 4-Methyl-2-[(3-oxo-1-buten-1-yl) amino]-5-phenylthiophene-3-carboxylic Acid Ethyl Ester From 2-amino-4-methyl-5-phenylthiophene-3-carboxylic acid ethyl ester (5 g) and commercially available 4-methoxy-3-buten-2-one (2.55 g), the title compound (6.06 g) was obtained similarly as in Example 13.

m.p. 111–114° C.

EXAMPLE 20

Production of 5-Acetyl-4-hydroxy-3-methyl-2-phenylthieno[2,3-b]pyridine

From the compound obtained in the above Example 19 (1 g), the title compound (0.754 g) was obtained similarly as in Example 14.

$^1$HNMR (300 MHz, CDCl$_3$)δ; 2.65(3H,s), 2.73(3H,s), 7.35–7.60(5H,m), 8.80(1H,s), 13.81(1H,s).

EXAMPLE 21

Production of 4-Methyl-2-[(3-oxo-3-phenyl-1-propen-1-yl)amino]-5-phenylthiophene-3-carboxylic Acid Ethyl Ester From 2-amino-4-methyl-5-phenylthiophene-3-carboxylic acid ethyl ester (1 g) and 3-methoxy-1-phenyl-2-propen-1-one (0.93 g), the title compound (1.166 g) was obtained similarly as in Example 13.

m.p. 106–108° C.

EXAMPLE 22

Production of 5-Benzoyl-4-hydroxy-3-methyl-2-phenylthieno[2,3-b]pyridine

From the compound obtained in Example 21 (1 g), the title compound (0.727 g) was obtained similarly as in Example 14.

m.p. 159–161° C. (recrystallized from acetonitrile).

EXAMPLE 23

Production of 5-(4-Methoxyphenyl)-4-methyl-2-[(4-methyl-3-oxo-1-penten-1-yl)amino]thiophene-3-carboxylic Acid Ethyl Ester From 2-amino-5-(4-methoxyphenyl)-4-methylthiophene-3-carboxylic acid ethyl ester [m.p. 84–86° C., obtained in a manner similar to that described in WO 95/28405 (JP-A-8-295693)] (1 g), the title compound (0.872 g) was obtained similarly as in Example 13.

m.p. 121–122° C.

EXAMPLE 24

Production of 4-Hydroxy-5-isobutyryl-2-(4-methoxyphenyl)-3-methylthieno[2,3-b]pyridine From the compound obtained in Example 23 (0.5 g), the title compound (0.327 g) was obtained similarly as in Example 14.

m.p. 129–133° C.

EXAMPLE 25

Production of 7-(2,6-Difluorobenzyl)-4,7-dihydro-5-isobutyryl-2-(4-methoxyphenyl)-3-methyl-4-oxothieno[2,3-b]pyridine From the compound obtained in Example 24 (0.25 g), the title compound (0.32 g) was obtained similarly as in Example 29 described below.

m.p. 183–186° C.

EXAMPLE 26

Production of 4-Methyl-2-[(4-methyl-3-oxo-1-penten-1-yl)amino]-5-(4-nitrophenyl)thiophene-3-carboxylic Acid Ethyl Ester 2-amino-4-methyl-5-(4-nitrophenyl)thiophene-3-carboxylic acid ethyl ester [m.p. 168–171° C., obtained in a manner similar to that described in WO 95/28405 (JP-A-8-295693)] was produced and the resultant compound (2.95 g) was subjected to the similar method as Example 13 to obtain the title compound (3.24 g, 83.4%).

m.p. 117–119° C.

EXAMPLE 27

Production of 5-(4-Isobutyrylaminophenyl)-4-methyl-2-[(4-methyl-3-oxo-1-penten-1-yl) aminolthiophene-3-carboxylic Acid Ethyl Ester From the compound obtained-in the above Example 12 (2 g), the title compound (2.43 g, 95.1%) was obtained similarly as in Example 13.

m.p. 181–184° C.

EXAMPLE 28

Production of 4-Hydroxy-5-isobutyryl-2-(4-isobutyrylaminophenyl)-3-methylthieno[2,3-b] pyridine The compound obtained in Example 27 (1.236 g) and diphenylether (12 ml) were mixed and the mixture was heated under reflux for 7 hours. After allowing to cool, the crystal precipitated was recovered by a filtration, washed with diisopropylether to obtain the title compound (0.798 g).

m.p. 247–249° C.

EXAMPLE 29

Production of 7-(2,6-Difluorobenzyl)-4,7-dihydro-5-isobutyryl-2-(4-isobutyrylaminophenyl)-3-methyl-4-oxothieno[2,3-b]pyridine The compound obtained in Example 28 (1 g), potassium carbonate (0.349 g) and N,N-dimethylformamide (5 ml) were mixed and 2,6-difluorobenzyl bromide (0.783 g) was added and the reaction mixture was stirred at room temperature overnight (15 hours). The reaction mixture was concentrated under reduced pressure to obtain a residue, which was partitioned between ethyl acetate-methyl ethyl ketone and water, and the aqueous layer was extracted with ethylacetate. The organic layers were combined and washed with a saturated saline and then dried over anhydrous magnesium sulfate. The residue obtained after concentration was washed with diisopropylether to obtain the title compound (1.2 g, 91.0%).

m.p. 219–222° C.

EXAMPLE 30

Production of 4,5,6,7-Tetrahydro-2-[(4-methyl-3-oxo-1-penten-1-yl)amino]benzo[b]thiophene-3-carboxylic Acid Ethyl Ester From a commercially available ethyl 2-amino-4,5,6,7-tetrahydrobenzo[b]thiophene-3-carboxylate (1 g), the title compound (1.384 g) was obtained similarly as in Example 13.

m.p. 78–80° C.

EXAMPLE 31

Production of 4,5,6,7-Tetrahydro-1-hydroxy-2-isobutyryl[1]benzothiolo[2,3-b]pyridine From the compound obtained in Example 30 (1 g), the title compound (0.645 g) was obtained similarly as in Example 14.

m.p. 156–159° C.

EXAMPLE 32

Production of 4-Methyl-2-[(4-methyl-3-oxo-1-penten-1-yl)amino]-5-phenylthiophene-3-carboxylic Acid Ethyl Ester 2-Amino-4-methyl-5-phenylthiophene-3-carboxylic acid ethyl ester [m.p. 93–95° C., a compound obtained by a method similar to that described in WO 95/28405 (JP-A-8-295693), hereinafter the same is applied analogously.] (50 g), 1-methoxy-4-methyl-1-penten-3-one (31 g), p-toluenesulfonic acid monohydrate (1.1 g) and toluene (500 ml) were mixed and the reaction mixture was stirred at room temperature for 6 hours. The reaction mixture was diluted with methyl ethyl ketone (170 ml), and washed with a saturated aqueous solution of sodium hydrogencarbonate, and the aqueous layer (wash) was extracted with a 3:1 mixture (200 ml) of ethyl acetate and methyl ethyl ketone. The organic layers were combined and washed with a saturated saline (300 ml) and then dried over anhydrous magnesium sulfate (20 g). The residue after concentration (precipitated crystal) was triturated with hexane (300 ml) and the mixture was stirred at room temperature for 1 hour and then with cooling at 10° C. for further 1 hour, and subsequently the crystal was recovered by a filtration, washed with hexane (200 ml) which was cooled at 10° C., and then dried in vacuo at 40° C. for 5 hours to obtain the title compound (60.2 g, 88.0%).

m.p. 104–108° C.

EXAMPLE 33

Production of 4-Hydroxy-5-isobutyryl-3-methyl-2-phenylthieno[2,3-b]pyridine

A compound obtained in an example, 4-methyl-2-[(4-methyl-3-oxo-1-penten-1-yl)amino]-5-phenylthiophene-3-carboxylic acid ethyl ether (50 g) and diphenylether (500 ml) were mixed and the reaction mixture was heated under reflux for 5.5 hours while removing the ethanol, which was formed as the reaction proceeded, by means of a distillation. After distilling diphenylether of f under reduced pressure followed by allowing to cool to about 100° C., at which time (before solidification), a water-containing 90% ethanol (250 ml) was added and the mixture was heated under reflux for 30 minutes. After allowing the mixture to cool followed by stirring with cooling on ice for 1 hour, the crystal precipitated was recovered by a filtration, washed with an ice-cooled water-containing 90% ethanol (200 ml), dried in vacuo at 40° C. for 5 hours to obtain the title compound (35.8 g, 82.2%).

m.p. 115–117° C.

EXAMPLE 34

Production of 7-(2,6-Difluorobenzyl)-4,7-dihydro-5-isobutyryl-3-methyl-4-oxo-2-phenylthieno[2,3-b]pyridine 4-Hydroxy-5-isobutyryl-3-methyl-2-phenylthieno[2,3-b]pyridine (35 g), potassium carbonate (18.6 g) and N,N-dimethylformamide (280 ml) were mixed and 2,6-difluorobenzyl bromide (27.9 g) was added and the reaction mixture was stirred at 40 to 50° C. for 2 hours. The reaction mixture was treated dropwise with water (560 ml), and the mixture was stirred for 1 hour and then cooled on ice, and then stirred further for 1 hour. The crude crystal was recovered by a filtration, washed with water (about 1000 ml), dried in air, suspended in a 1:1 solvent mixture (250 ml) of ethyl acetate and diisopropylether, and then the mixture was stirred at room temperature for 1 hour, and then stirred with cooling on ice for 1 hour. The crystal obtained by a filtration was washed with the same solvent mixture (180 ml), dried in vacuo at 40° C. for 5 hours to obtain the title compound (46.53 g, 94.6%).

m.p. 205–207° C.

EXAMPLE 35

Production of 3-Bromomethyl-7-(2,6-difluorobenzyl)-4,7-dihydro-5-isobutyryl-4-oxo-2-phenylthieno[2,3-b]pyridine 7-(2,6-Difluorobenzyl-4,7-dihydro-5-isobutyryl-3-methyl-4-oxo-2-phenylthieno[2,3-b]pyridine (46 g), N-bromosuccinimide (22.5 g), azobisisobutyronitrile (1.73 g) and ethyl acetate (460 ml) were mixed and the reaction mixture was heated under reflux for 2 hours. The reaction mixture was allowed to cool with stirring over a period of 2 hours, and then stirred with cooling on ice for 1.5 hours, the precipitated crystal was recovered by a filtration, and washed with a 1:1 solvent mixture (320 ml) of ice-cooled hexane and ethyl acetate and water (300 ml), dried in vacuo at 40° C. for 6 hours to obtain the title compound (40.82 g, 75.2%).

m.p. 189–192° C.

EXAMPLE 36

Production of 3-Bromomethyl-7-(2,6-difluorobenzyl)-4,7-dihydro-5-isobutyryl-4-oxo-2-phenylthieno[2,3-b]pyridine 7-(2,6-Difluorobenzyl)-4,7-dihydro-5-isobutyryl-3-methyl-4-oxo-2-phenylthieno[2,3-b]pyridine (10 g), N-bromosuccinimide (4.86 g), 2,2'-azobis(2,4-dimethylvaleronitrile (0.56 g) and methyl acetate (100 ml) were mixed and the reaction mixture was heated under reflux for 2 hours. The reaction mixture was allowed to cool with stirring over a period of 2 hours, water (50 ml) was added and then the mixture was stirred with cooling on ice for 1.5 hours. The crystal precipitated was recovered by a filtration, washed with an ice-cooled methyl acetate (30 ml) and water (30 ml), dried in vacuo at 40° C. for 6 hours to obtain the title compound (10.61 g, 87.1%).

m.p. 189–192° C.

EXAMPLE 37

Production of 3-Bromomethyl-7-(2,6-difluorobenzyl)-4,7-dihydro-5-isobutyryl-2-(4-nitrophenyl)-4-oxothieno[2,3-b]pyridine 3-Bromomethyl-7-(2,6-difluorobenzyl)-4,7-dihydro-5-isobutyryl-4-oxo-2-phenylthieno[2,3-b]pyridine (40 g) was dissolved in methanesulfonic acid (200 ml) with cooling at 13 to 15° C. and then treated dropwise with a solution of sodium nitrate (6.59 g) in methanesulfonic acid (100 ml) over a period of 1 hour. The mixture was stirred as it was for 2.5 hours, and then poured into a cool water (2800 ml), and the crystal precipitated was recovered by a filtration, washed with water until the pH of the wash became 5 to 6, and then dried in vacuo at 50° C. for 24 hours. The rude crystal thus obtained was suspended in ethyl acetate (300 ml), and the reaction mixture was stirred at 50° C. for 1 hour and then with cooling on ice for 1 hour, and the crystal was recovered by a filtration, washed with a cooled ethyl acetate (100 ml), dried in vacuo at 40° C. for 5 hours to obtain the title compound (32.4 g, 74.5%).

m.p. 202–204° C.

EXAMPLE 38

Production of 3-(N-Benzyl-N-methylaminomethyl)-7-(2,6-difluorobenzyl)-4,7-dihydro-5-isobutyryl-2-(4-nitrophenyl)-4-oxothieno[2,3-b]pyridine 3-bromomethyl-7-(2,6-difluorobenzyl)-4,7-dihydro-5-isobutyryl-2-(4-nitrophenyl)-4-oxothieno[2,3-b]pyridine (32 g), N,N-dimethylformamide (64 ml) and N-ethyldiisopropylamine (8.84 g) were mixed and treated dropwise with N-methylbenzylamine (8.29 g) with cooling on ice, and the reaction mixture was stirred at 30 to 40° C. for 5 hours. The reaction mixture was poured into a mixture of a solution of potassium carbonate (9.5 g) in water (320 ml) and diisopropylether (320 ml) and the reaction mixture was stirred at room temperature for 2 hours and then with cooling on ice for 1 hour, and the crystal precipitated was recovered by a filtration, washed with water (600 ml) and diusopropylether (160 ml), dried in vacuo at 50° C. for 4 hours to obtain the title compound (33.58 g, 97.9%).

m.p. 158–162° C.

EXAMPLE 39

Production of 2-(4-Aminophenyl)-3-(N-benzyl-N-methylaminomethyl)-7-(2,6-difluorobenzyl)-4,7-dihydro-5-isobutyryl-4-oxothieno[2,3-b]pyridine Fumarate 3-(N-Benzyl-N-methylaminomethyl)-7-(2,6-difluorobenzyl)-4,7-dihydro-5-isobutyryl-2-(4-nitrophenyl)-4-oxothieno[2,3-b]pyridine (33 g), iron powder (12.3 g) and ethanol (132 ml) were mixed and treated dropwise with concentrated hydrochloric acid (55.5 g) diluted with water (19 ml) over a period of 2 hours with cooling on ice, and the reaction mixture was stirred as it was for 2 hours. The reaction mixture was poured into a solution of sodium hydrogencarbonate (55.3 g) in water (450 ml) and the mixture was stirred for 1 hour together with ethyl acetate (825 ml), and filtered through a Hyflo Super Cell to remove insoluble materials. The aqueous layer was extracted with ethyl acetate (500 ml) and then the organic layers were combined, and washed with a saturated saline (1000 ml), dried over anhydrous magnesium sulfate (35 g) and then concentrated into dryness to obtain a crude product of 2-(4-aminophenyl)-3-(N-benzyl-N-methylaminomethyl)-7-(2,6-difluorobenzyl)-4,7-dihydro-5-isobutyryl-4-oxothieno[2,3-b]pyridine (32.3 g). This was dissolved in methanol (200 ml) and admixed with a solution of fumaric acid (6.56 g) in methanol (200 ml) and the mixture was concentrated under reduced pressure to about 150 g. The precipitated suspension thus obtained was diluted with ethyl acetate (300 ml) and the mixture was stirred at room temperature for 1 hour and then the crystal was recovered by a filtration. After washing with ethyl acetate (200 ml) followed by drying in vacuo at 50° C. for 3 hours, the title compound (33.38 g, 88.5%) was obtained.

m.p. 222–225° C.

EXAMPLE 40

Production of 2-(4-Aminophenyl)-3-(N-benzyl-N-methylaminomethyl)-7-(2,6-difluorobenzyl)-4,7-dihydro-5-isobutyryl-4-oxothieno[2,3-b]pyridine Trimethanesulfonate From the crude product of 2-(4-aminophenyl)-3-(N-benzyl-N-methylaminomethyl)-7-(2,6-difluorobenzyl)-4,7-dihydro-5-isobutyryl-4-oxothieno[2,3-b]pyridine obtained in Example 39 (500 mg) and methanesulfonic acid (168 mg), the title compound (619 mg, 82.3%) was obtained similarly as in Example 39. However, as a solvent, ethanol was used instead of methanol.

m.p. 131–135° C.

EXAMPLE 41

Production of 2-(4-Aminophenyl)-3-(N-benzyl-N-methylaminomethyl)-7-(2,6-difluorobenzyl)-4,7-dihydro-5-isobutyryl-4-oxothieno2,3-b]pyridine Oxalate From the crude product of 2-(4-aminophenyl)-3-(N-benzyl-N-methylaminomethyl)-7-(2,6-difluorobenzyl)-4,7-dihydro-5-isobutyryl-4-oxothieno[2,3-b]pyridine obtained in Example 39 (500 mg) and oxalic acid (79 mg), the title compound (499 mg, 82.6%) was obtained similarly as in Example 40.

m.p. 159–163° C.

EXAMPLE 42

Production of 2-(4-Aminophenyl)-3-(N-benzyl-N-methylaminomethyl)-7-(2,6-difluorobenzyl)-4,7-dihydro-5-isobutyryl-4-oxothieno[2,3-b]pyridine Malonate From the crude product of 2-(4-aminophenyl)-3-(N-benzyl-N-methylaminomethyl)-7-(2,6-difluorobenzyl)-4,7- dihydro-5-isobutyryl-4-oxothieno[2,3-b]pyridine obtained in Example 39 (500 mg) and malonic acid (91 mg), the title compound (533 mg, 90.2%) was obtained similarly as in Example 40.

m.p. 144–146° C.

EXAMPLE 43

Production of 2-(4-Aminophenyl)-3-(N-benzyl-N-methylaminomethyl)-7-(2,6-difluorobenzyl)-4,7-dihydro-5-isobutyryl-4-oxothieno[2,3-b]pyridine Succinate From the crude product of 2-(4-aminophenyl)-3-(N-benzyl-N-methylaminomethyl)-7-(2,6-difluorobenzyl)-4,7-dihydro-5-isobutyryl-4-oxothieno[2,3-b]pyridine obtained in Example 39 (500 mg) and succinic acid (103 mg), the title compound (573 mg, 95.0%) was obtained similarly as in Example 40.

m.p. 183–188° C.

EXAMPLE 44

Production of 2-(4-Aminophenyl)-3-(N-benzyl-N-methylaminomethyl)-7-(2,6-difluorobenzyl)-4,7-dihydro-5-isobutyryl-4-oxothieno[2,3-b]pyridine Malate From the crude product of 2-(4-aminophenyl)-3-(N-benzyl-N-methylaminomethyl)-7-(2,6-difluorobenzyl)-4,7-dihydro-5-isobutyryl-4-oxothieno[2,3-b]pyridine obtained in Example 39 (500 mg) and malic acid (117 mg), the title compound (545 mg, 88.3%) was obtained similarly as in Example 40.

m.p. 169–174° C.

The chemical structures of the compounds obtained in the above Examples 13 to 15 and 19 to 31 are shown in Table 2 to Table 4.

TABLE 2

| Ex. No. | $R^1$ | $R^2$ | $R^3$ |
|---|---|---|---|
| 13 | methyl | phenyl | isopropyl |
| 19 | methyl | phenyl | methyl |
| 21 | methyl | phenyl | phenyl |
| 23 | methyl | 4-methoxyphenyl | isopropyl |
| 26 | methyl | 4-nitrophenyl | isopropyl |
| 27 | methyl | 4-isobutyrylaminophenyl | isopropyl |
| 30 | | cyclohexenyl | isopropyl |

TABLE 3

| Ex. No. | $R^1$ | $R^2$ | $R^3$ |
|---|---|---|---|
| 14 | methyl | phenyl | isopropyl |
| 20 | methyl | phenyl | methyl |
| 22 | methyl | phenyl | phenyl |
| 24 | methyl | 4-methoxyphenyl | isopropyl |
| 28 | methyl | 4-isobutyrylaminophenyl | isopropyl |
| 31 | | cyclohexenyl | isopropyl |

TABLE 4

| Ex. No. | $R^{22}$ |
|---|---|
| 15 | hydrogen |
| 25 | methoxy |
| 29 | isobutyrylamino |

INDUSTRIAL APPLICABILITY

According to the present invention, an intermediate for a thienopyridine derivative useful as a GnRH antagonist can be produced at a high yield.

Thus, by haloganating the hydrocarbon in the 3-position of a thienopyridine derivative followed by nitrating, the use of carbon tetrachloride which has been essential can be avoided, and a nitro form can safely be produced under a gentle condition.

By converting a compound having a carboxylic acid in the 5-position of a thienopyridine derivative into an acid amide derivative which was then converted into a ketone body, the use of a dangerous trimethylaluminum can be avoided, and a target product can safely be produced.

Also according to the invention, 5-acyl-4-hydroxythieno [2,3-b]pyridine skeleton useful as an intermediate for a pharmaceutical can be produced in a simple process at a high yield.

What is claimed is:

1. A compound of the formula:

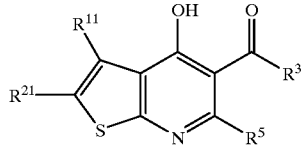

wherein $R^{11}$ represents $C_{1-6}$ alkyl, $R^{21}$ represents phenyl which may be substituted, or $R^{11}$ and $R^{21}$ form, taken together with adjacent two carbon atoms, a 5- to 7-membered ring which may be substituted, $R^3$ represents a hydrocarbon group which may be substituted, and $R^5$ represents hydrogen or a hydrocarbon group, or a salt thereof.

2. A compound of claim 1 or a salt thereof, wherein the substituent of the phenyl which may be substituted for $R^{21}$ is isobutyrylamino or methoxy.

3. A compound of claim 1 or a salt thereof, which is 4-hydroxy-5-isobutyryl-3-methyl-2-phenylthieno[2,3-b]pyridine.

4. A compound of claim 1 or a salt thereof, which is 4-hydroxy-5-isobutyryl-2-(4-isobutyrylaminophenyl)-3-methylthieno[2,3-b]pyridine.

* * * * *